(12) United States Patent
Shaw et al.

(10) Patent No.: US 7,772,388 B2
(45) Date of Patent: Aug. 10, 2010

(54) INHIBITION OF METALLO-β-LACTAMASE

(75) Inventors: Robert W. Shaw, Lubbock, TX (US); Sung-Kun Kim, Lubbock, TX (US)

(73) Assignee: Texas Tech University, Lubbock, TX (US)

(*) Notice: Subject to any disclaimer, the term of this patent is extended or adjusted under 35 U.S.C. 154(b) by 0 days.

(21) Appl. No.: 12/237,241

(22) Filed: Sep. 24, 2008

(65) Prior Publication Data

US 2009/0203003 A1 Aug. 13, 2009

Related U.S. Application Data

(62) Division of application No. 10/527,725, filed as application No. PCT/US03/28782 on Sep. 12, 2003, now Pat. No. 7,456,274.

(60) Provisional application No. 60/411,118, filed on Sep. 16, 2002.

(51) Int. Cl.
*C07H 21/04* (2006.01)
*C12Q 1/64* (2006.01)
*C40B 30/04* (2006.01)
*C40B 40/04* (2006.01)
*C40B 40/06* (2006.01)

(52) U.S. Cl. .............. 536/24.3; 435/6; 506/9; 506/15; 506/16

(58) Field of Classification Search ............ None
See application file for complete search history.

(56) References Cited

U.S. PATENT DOCUMENTS 5,705,340 A * 1/1998 Rasmussen et al. ............ 435/6
7,456,274 B2 11/2008 Shaw

OTHER PUBLICATIONS

Allawi, H. T. And SantaLucia, J. Jr. (1997), "Thermodynamics and NMR of Internal G-T Mismatches in DNA", Biochemistry 36, 10581-10594.
Ambler, R. P., Daniel, M., Fleming, J., Hermoso, J. -M., Pang, C. and Waley, S. G. (1985), "The Amino Acid Sequence of the Zinc-Requiring β-Lactamase II from the bacterium Bacillus cereus", FEBS Lett. 189, 207-211.
Bartel, D. P. and Szostak, 1. W., (1993), "Isolation New Ribozymes from a Large Pool of Random Sequences", Science 261, 1411-1418.
Bicknell, R., Schaeffer, A., Waley, S. G. and Auld, D. S. (1986), "Changes in the Coordination Geometry of the Active-Site Metal During Catalysis of Benzylpenicillin Hydrolysis by Bacillus cereus β-Lactamase II", Biochemistry 25, 7208-7215.
Bock, L. C., Griffin, L. c., Latham, J. A., Vermass, E. H. and Toole, J. J. (1992), "Selection of Single-Stranded DNA Molecules that bind and Inhibit Human Thrombin", Nature 355, 564-566.
Chen, H. and Gold, L, (1994), "Selection of High-Affinity RNA Ligands to Reverse Transcriptase", Biochemistry 33, 8746-8756.
Concha, N. 0., Janson, C. A., Rowling, P., Pearson, S., Cheever, C. A., Clarke, B. P., Lewis, C., Galleni, M., Frere, J. M., Payne, D. J., Bateson, J. H. and Abdel-Meguid, S. S. (2000), "Crystal of the IMP-I Metallo-β-Lactamase from Pseudomonas aeruginosa and its Complex with a Mercaptocarboxvlate Inhibitor", Biochemistry 15, 4288-4298.
Crompton, B., Jago, M., Crawford, K., Newton, G. G. F. and Abraham, E. P. (1962), "Behaviour of Some Derivatives of 7-Aminocephalosporanic Acid as Substrates, Inhibitors and Inducers of Penicillanases", Biochem. J. 83, 52-63.
Davies, R. B. and Abraham, E. P. (1974), "Metal Cofactor Requirements of β-Lactamase II", Biochem. J. 143, 129-135.
Davies, R. B. Abraham, E. P. and Melling, J. (1974), "Separation, Purification and Properties of β-Lactamase I and β-Lactamase II from Bacillus cereus 569/H/9", Biochem. J. 143, 115-127.
Davies, R. B. Abraham, E. P. Melling, J. and Pollock, M. R. (1975),"Comparison of β-lactamase II from Bacillus cereus 569/H/9 with a β-Lactamase from Bacillus cereus 51B/6", Biochem. J. 145,409-411.
Farmulok, M. and Szostak, J. W. (1992), "In Vitro Selection of Specific Ligand Binding Nucleic Acids", Angew. Chem. Int. Ed. Engl. 31, 979-988.
Felici, A. and Amicosante, G. (1995), "Kinetic Analysis of Extension of Substrate Specificity with Xanthomonas maltophilia, Aeromonas hydrophylia and Bacillus cereus Metallo-β-Lactamases", Antimicrob. Agents Chemother. 39, 192-199.
Felici, A, Amicosante, G., Oratore, A, Strom, R., Ledent, R, Joris, B., Fanuel, L. and Frere, J. -M. (1993), "An Overview of the Kinetic Parameters of Class B β-Lactamases", Biochem. J. 291, 151-155.
Felici, A, Perilli, M., Franceschini, N., Rossolini, G. M., Galleni, M., Frere, J. -M., Oratore, A and Amicosante, G. (1997), "Sensitivity of Aeromonas hydrophilia Carbapenemase to ΔΑ3-Cephems", Antimicrob. Agents Chemother. 41, 866-868.
Hicke, B. J. and Stephens, A. W. (2000), "Escort Aptamers", J. Clin. Invest. 106, 923-928.
Hilliard, N. P., (1995), "Structure-Function Relationships in the Metallo-β-Lactamase of Bacillus cereus 5/B/6", Ph.D. thesis, Texas Tech University.
Hussain, M., Pastor, F. I. J. and Lampen, J. O. (1987), "Cloning and Sequencing of the blaZ Gene Encoding β-Lactamase III, a Lipoprotein of Bacillus cereus 569/H", J. Bacteriol. 169, 579-586.

(Continued)

*Primary Examiner*—Young J Kim
(74) *Attorney, Agent, or Firm*—Roman Aguilera, III

(57) ABSTRACT

A method to identify a high affinity nucleic acid ligand to inhibit the activity of a lactamase enzyme. The method comprises several steps that initially involve preparing a candidate mixture of nucleic acids. The candidate mixture of nucleic acids is then allowed to make contact with the lactamase enzyme under controlled conditions of temperature, ionic strength and pH; the combination forms a candidate-enzyme mixture. The target nucleic acids are partitioned from the remainder of the candidate mixture. The target nucleic acids that have been partitioned are amplified to yield a pool of nucleic acids enriched with target nucleic acid sequences. The enriched pool of target nucleic acids have a relatively higher affinity and specificity for binding to the lactamase, whereby nucleic acid ligand of the lactamase are identified. Nucleic acid ligands that inhibit an activity of lactamase. The lactamase includes class B, metallo-β-lactamase.

5 Claims, 21 Drawing Sheets

OTHER PUBLICATIONS

Jaeger, J. A., Turner, D. H. and Zuker, M. (1989), "Improved Predictions of Secondary Structures for RNA", Proc. Natl. Acad. Sci. USA 86, 7706-7710.

Jaeger, J. A, Turner, D. H. and Zuker, M. (1990), "Predicting Optimal and Suboptimal Secondary Structure for RNA", in Methods in Enzymology 183, 281-306.

Jellinek, D., Green, L. S., Bell, C. and Janjic, N. (1994), "Inhibition of Receptor Binding by High-Affinity RNA Ligands to Vascular Endothelial Growth Factor", Biochemistry 33, 10450-10456.

Kogut, M., Pollock, M. R. and Tridgell, E. J. (1956), "Purification of Penicillin-Induced Penicillinase of Bacillus cereus NRRL 569", Biochem. J. 62, 391-401.

Kuwabara, S., Adams, E. P. and Abraham, E. P. (1970),"Composition of β-lactamase I and β-Lactamase II from Bacillus cereus 569/H", Biochem. J. 118, 475-480.

Kuwabara, S. and Lloyd, P. H. (1971), "Protein and Carbohydrate Moieties of a Preparation of β-Lactamase II", Biochem. J. 124, 215-220.

Ledent, R, Raquet, X., Joris, B., Van Beeumen, J. and Frere, 1. -M. (1993), "A Comparative Study of Class D Beta-Lactamases", Biochem. J. 292, 555-562.

Lim, H. M., Pene, J. J. and Shaw, R. W. (1988), "Cloning, Nucleotide Sequence and Expression of the Bacillus cereus 51B16 β-Lactamase II Structural Gene" 1. Bacteriol. 170, 2873-2878.

Macaya, R. F., Waldron, J. A, Beutel, B. A., Gao, H., Joeston, M. E., Yang, M., Patel, R., Bertelsen, A. H. and Cook, A G. (1995), "Structural and Functional Characterization of Potent Antithrombotic Oligonucleotides Possessing Both Quadruplex and Duplex Motifs", Biochemistry 34, 4478-4492.

Matagne, A., Ledent, P., Monnaie, D., Felici, A., Jamin, M., Raquet, X., Galleni, M., Klein, D., Francois, Land Frere, J. M. (1995), "Kinetic Study of Interaction Between BRL 42715, β-Lactamases and D-Alanyl-D-Alanyl Peptidases", Antimicrob. Agents Chemother. 39, 227-231.

Neu, H. C. (1992), "The Crisis in Antibiotic Resistance", Science 257, 1064-1073.

Payne, D. J. (1993),"Metallo-β-lactamases-A New Therapeutic Challenge", J. Med. Microbiol. 39, 993-999.

Rasmussen, B. A., Yang, Y., Jacobs, N. and Bush, K. (1994), "Contribution of Enzymatic Properties, Cell Permeability and Enzyme Expression to Microbial Activities of Beta-lactams in Three Bacteroides fragilis Isolates that Harbor a Metallo-β-Lactamase gene", Antimicrob. Agents Chemother. 38, 2116-2120.

Robertson, D. L. and Joyce, G. F. (1990), "Selection in vitro of an RNA Enzyme that Specifically Cleaves Single-Stranded DNA", Nature 344, 467-468.

Ruckman, J., Green, L. S., Beeson, J., Waugh, S., Gillette, W. L., Henninger, D. D., Claesson-Welsh, L. and Janjic, N. (1998), "2'-Fluoropyrimidine RNA-Based Aptamers to the 165-Amino Acid Form of Vascular Endothelial Growth Factor (VEGF165)", Journal of Biological Chemistry 273, 20556-20567.

Sabath, L. D. and Abraham, E. P. (1966), "Zinc as a Cofactor for Cephalosporinase from Bacillus cereus 569", Biochem. J. 98, 11c-13c.

Sutton, B. J., Artymiuk, P. J., Cordero-Borboa, A. E., Little, C., Philips, D. C. and Waley, S. G. (1987), "X-Ray Crystallographic Study of β-Lactamase II from Bacillus cereus at 0.35 nm Resolution", Biochem. J. 248, 181-188.

Tasset, D. M., Kubik, M. F. and Steiner, W. (1997), "Oligonucleotide Inhibitors of Human Thrombin that Bind Distinct Epitopes", J. Mol. Biol. 272, 688-698.

Thatcher, D. R. (1975), "Partial Amino Acid Sequence of the Extracellular β-Lactamase I of Bacillus cereus 569/H", Biochem. J. 147, 313-326.

Tsiang, M., Gibbs, C. S., Griffin, L. C., Dunn, K. E. and Leung, L. K. (1995), "Selection of a Suppressor mutation That Restores Affinity of an Oligonucleotide Inhibitor for Thrombin Using in Vitro Genetics", J. Biol. Chem. 270, 19370-19376.

Tuerk, C. and Gold, L. (1990), "Systematic Evolution of Ligands by Exponential Enrichment", Science 249, 505-510.

Turner, D. H., Sugimoto, N. and Freier, S. M. (1988), "RNA Structure Prediction", Annu. Rev. Biophys. Biophys. Chem. 17, 167-192.

Zuber, M., Patterson, T. A. and Court, D. L. (1987),"Analysis of nutR", Proc. Natl. Acad. Sci. USA 84, 4514-4518.

Zuker, M. (1989), "On Finding All Suboptimal Foldings of an RNA Molecule", Science 244, 48-52.

Pitout J. D., Sanders C. C., Sanders W. E. Jr. (1997), "Antimicrobial Resistance with Focus on Beta-lactam Resistance in Gram-Negative Bacilli", Am. J. Med. 103(1): 51-9.

* cited by examiner

PENICILLINS

PENICILLINS

PENICILLINS

DALANYL-D-ALANINE-PEPTIDOGLYCAN

```
                        A C
                       A   T
                       A·T
                       C·G
                   5'AACC·G
                          A
                          T
                  3'A A G·C
                      T C·G  G
                      G       T
                       T      G
                        A    C
                         C A
```

INHIBITION OF METALLO-β-LACTAMASE

CROSS-REFERENCE TO RELATED APPLICATION

This application is a divisional of U.S. application Ser. No. 10/527,725, filed Mar. 14, 2005 now U.S. Pat. No. 7,456,274, which is a §371 application of PCT International Patent Application Number PCT/US03/28782 filed Sep. 12, 2003, which claims priority to U.S. Provisional Application No. 60/411,118, filed Sep. 16, 2002.

INTRODUCTION

One aspect of the current invention is a method for identifying a high affinity nucleic acid ligand to inhibit the activity of a lactamase enzyme. The method comprises several steps that initially involve preparing a candidate mixture of nucleic acids. The candidate mixture of nucleic acids is then allowed to make contact with the lactamase enzyme under controlled conditions of temperature, ionic strength and pH; the combination forms a candidate-enzyme mixture. Not all candidates bind tightly to the enzyme. The target nucleic acids may be easily partitioned from the remainder of the candidate mixture. Partitioning the target-nucleic acids from the remainder of the candidate mixture can be performed by many methods known to one skilled in the art. Once the target nucleic acids have been partitioned, they can be amplified to yield a pool of nucleic acids enriched with target nucleic acid sequences. The enriched pool of target nucleic acids have a relatively higher affinity and specificity for binding to the lactamase, whereby nucleic acid ligand of the lactamase may be identified through methods known to one skilled in the art of molecular biology (e.g. DNA sequencing).

Another aspect of the current invention involves nucleic acid ligands that inhibit an activity of lactamase. In a preferred embodiment, the lactamase is a class B, metallo-β-lactamase. Another preferred embodiment includes specific nucleic acid ligands that inhibit B. cereus 5/B/6 metallo-β-lactamase. Yet another preferred embodiment includes specific nucleic acid ligands that inhibit B. cereus 569/H/9 metallo-β-lactamase.

β-lactam antibiotics: The β-lactam antibiotics are analogs of a peptidoglycan that is involved in bacterial cell wall synthesis. Common examples of β-lactam antibiotics are penicillins, cephalosporins, monobactams and carbapenems. The targets of the β-lactam antibiotics are D-alanyl-D-alanine carboxypepidases/transpeptidases ("DD-peptidases") that catalyze the formation of the peptide cross-links of the peptidoglycan in the final stages of the bacterial cell wall synthesis. The β-lactam antibiotics inhibit DD-peptidases by forming a stable covalent acyl-enzyme complex with the enzyme that has a longer half-life than that formed with the peptidoglycan, thus disrupting the construction of the bacterial cell wall, thereby causing the death of bacteria (Kelly et al., 1988; Ghuysen, 1988). Antibacterial agents typically have easy access to the external surface of the cytoplasmic membrane, which is the site where bacterial cell wall synthesis occurs. Since the mammalian cells have a different membrane with no cell wall structures, the β-lactams are highly specific for bacteria and have few side effects even at high concentrations of β-lactam antibiotics (Maugh, 1981).

The general structures of penicillins and cephalosporins are shown in FIG. 2, and FIG. 3 shows the comparison of the structure of penicillins with the structure of D-alanyl-D-alanine-peptidoglycan (Suskoviae et al., 1991). When the β-lactam antibiotic compounds are held in a strained configuration by the ring system, the β-lactam and the adjacent atoms have a spatial configuration similar to that of peptidoglycan. Although not wanting to be bound by theory, it is this similarity that gives the antibiotics their bactericidal effects. Unfortunately, some bacteria have become resistant to such antibiotics. One defense that antibiotic resistant bacterium have acquired is an enzyme called β-lactamase (β-lactamhydrolyase, EC 3.5.2.6). β-lactamases are highly efficient enzymes that catalyze the hydrolysis of the β-lactam rings of antibiotics (e.g. penicillins, cephalosporins, monobactams and carbapenems) causing these compounds to quickly lose their bactericidal activity (Fisher et al., 1981; Maugh, 1981). The catalysis of hydrolysis of a generic β-lactam ring by a β-lactamases (Livermore, 1991) is shown in FIG. 1.

Bacteria that have acquired the genes for the production of β-lactamases are resistant to β-lactam antibiotics (Neu, 1992), and past research ideology on developing new β-lactam antibiotics has focused upon keeping ahead of the spread of the bacterial drug-resistance by making slight alterations in the structures of the existing β-lactam antibiotics. For example, cephalosporins have passed through four generations (Maugh, 1981; Pitout et al., 1997). But there are limits on utilizing chemical manipulation of the existing groups of antibiotics. Therefore, it is increasingly important to design new types of antibiotics and mechanism-based β-lactamase inhibitors, and to understand the mechanisms by which β-lactamases function. Although the use of β-lactam/β-lactamase inhibitor combinations has increased, the design of a therapeutically useful β-lactam antibiotics or inhibitors requires a more detailed understanding of the function of β-lactamases. Studies of the chemical reaction mechanisms of β-lactamases are of vital importance in designing new antibiotic compounds and new β-lactamase inhibitors (Abraham and Waley, 1979; Brenner and Knowles, 1984).

Classification of β-lactamases. Bacteria produce a wide range of β-lactamases. An incomplete list of bacteria that produce β-lactamases include Bacillus anthracis, Bacillus cereus, Bacillus fragilis, Escherichia coli, Aeromonous hydrophilia, Bacteroides, Staphylococcus epidermidis, Streptococcus, Pseudomonas aeruginosa, Providencia, Haemophilus, Xanthomonas maltophilia, Acinetobacter, Catrobacter, Enterobacter and Branhamella (Danziger and Pendland, 1995). β-lactamases are classified on the basis of their primary structures and catalytic properties. There are currently four classes of β-lactamases: class A, B, C and D (Ambler, 1980; Ambler et al., 1991; Joris et al., 1991; Frere, 1995). Class A, C and D β-lactamases are serine-active-site enzymes that resemble serine proteases and form an acyl-enzyme intermediate with an active-site serine during the catalysis of β-lactam antibiotics (Rahil and Pratt, 1991). Class A β-lactamases are soluble enzymes, and the class C β-lactamases are very similar to class A β-lactamases except they are membrane bound (Hussain et al., 1987). Class D β-lactamases do not exhibit primary sequence similarities to class A and C β-lactamases (Joris et al., 1991; Ledent et al., 1993). The class B β-lactamases, on the other hand, is quite different from the other classes of β-lactamases. These are metallo-β-lactamases, which require divalent metal ions for enzymatic activity (Ambler, 1980; Abraham and Waley, 1979). Native class B β-lactamases are isolated with one or two zinc ions bound to their active sites (Carfi et al., 1995; Concha et al., 1996).

The β-lactam antibiotics that are substrates of class B β-lactamases include penicillin derivatives and cephalosporin derivatives. (Felici et al., 1997; Felici and Amicosante, 1995; Felici et al., 1993). B. cereus 569/H/9 β-lactamase I is 8,800 times less active with cephalosporin C than the metallo-β-lactamase (Abraham and Waley, 1979). Hydrolysis of β-lactam antibiotics such as carbapenems, cephamycins and imipenem, which are normally resistant to the serine β-lactamase, is also catalyzed by the class B β-lactamases (Felic et al., 1993; Felici and Amicosante, 1995; Rasmussen et al., 1994). The inhibitors for other classes of β-lactamases such as penem, 6-β-iodopenicillanic acid, penicillanic acid sulfone and clavulanic acid do not inhibit class B β-lactamases (Felici and Amicosante, 1995; Matagne et al., 1995). Recently a series of mercaptoacetic acid thiol esters (Payne et al., 1997; Yang and Crowder, 1999) and thiomandelic acid Mollard et al., 2001) have been identified as metallo-β-lactamase inhibitors. Also, understanding the structure and dynamics of metallo-β-lactamases has been studied (Carfi et al., 1995; Concha et al., 1996; Scrofani et al., 1999; Concha et al., 2000). However, there is still a need to develop more effective inhibitors for metallo-β-lactamases.

Metallo-β-lactamases have been detected in an increasing number of pathogenic bacteria including *Anthracis, Bacillus, Bacteroides, Xanthomonas, Aeromonas, Pseudomonas, Stenotrophomonas, Klebsiella, Flavobacterium, Legionella, Enterobacter* and *Serratia* (Fecili and Amicosante, 1995; Payne, 1993; Payne et al., 1997). These findings underline the spreading of metallo-β-lactamases genes among pathogenic bacteria.

Metallo-β-lactamases from *B. cereus* 5/B/6. The first metallo-β-lactamase was identified in *B. cereus* 569 (Sabath and Abraham, 1966). It was shown that a part of the cephalosporinase activity in the crude penicillinase preparation from *B. cereus* strain 569 required $Zn^{2+}$ for maximum activity. This enzyme was reported to have unique thermal stability. Heating at 60° C. for 30 min. does not abolish the catalytic activity of this enzyme (Crompton et al., 1962; Davies et al., 1974). The first purified metallo-β-lactamases were reported to have been obtained by Kuwabara et al. (1970). From *B. cereus* 569/H, a spontaneous mutant of strain 569 produces class B β-lactamases constitutively (Kogut et al., 1956). The purification procedure was performed by Kuwabara and Lloyd (1971).

Another *B. cereus* strain (5/B) was found to produce one class A β-lactamase and one metallo-β-lactamase. This metallo-β-lactamase is very similar to the metallo-β-lactamases produced by *B. cereus* 569 and 569/H except with slightly different substrate specificity (Crompton et al., 1962). *B. cereus* 5/B/6, a mutant form of *B. cereus* 5/B, produces only the metallo-β-lactamase due to a mutation in the structural gene required for the synthesis of the class A β-lactamases (Davies et al., 1975; Abraham and Waley, 1979). The metallo-β-lactamases from *B. cereus* strain 5/B/6 was later purified in a similar manner as *B. cereus* 569/H/19 (Thatcher, 1975). The metallo-β-lactamases from these strains of *B. cereus*, which are isolated with one or two $Zn^{2+}$ ions at the active site, were among the first to be studied of the class B enzymes (Ambler, 1985; Bicknell et al., 1986; Sutton et al., 1987; Meyers and Shaw, 1989). The metallo-β-lactamases from these strains of *B. cereus* are very similar. They both consist of 227 amino acid residues among which 209 residues are identical (Limn et al., 1988). Although these β-lactamases are isolated with a $Zn^{2+}$ bound at the active site, other metal ions including $Co^{2+}$, $Cd^{2+}$, $Mn^{2+}$, $Hg^{2+}$ and $Cu^{2+}$ support some catalytic activity of the enzymes Davies and Abraham, 1974; Hilliard and Shaw, 1992; Hilliard, 1995).

The metallo-β-lactamases from *B. cereus* 569/H/9 and 5/B/6 are secreted extracellularly. The latter enzyme has a 29 amino acid leader sequence before it is secreted from the cell. The gene for this enzyme has been cloned, sequenced and characterized in great detail in *E. coli*. It has also been expressed as an intracellular enzyme with the signal sequence at relatively low levels in *E. coli* (Lim et al., 1988). It was also revealed that the metallo-β-lactamases from *B. cereus* strains 5/B/6 and 569/H/9 differ by only 18 amino acid residues (Lim et al., 1988). Even though the procedure for production and purification of this enzyme from *B. cereus* 5/B/6 cultures was greatly improved (Meyers and Shaw, 1989), hyperexpression in *E. coli* was still desirable. The construct used at that time did not achieve this goal (Lim et al., 1988). The main cause of the low levels of expression was postulated to be the presence of the 29 amino acid leader peptide at the 5' end of this β-lactamase which signals the secretion of the enzyme from the *B. cereus* cell (Shaw et al., 1991).

Site-directed mutagenesis was performed to remove the leader sequence and introduce a NdeI restriction endonuclease site (Shaw et al., 1991) at the initiator codon of the *B. cereus* 5/B/6 β-lactamase structural gene as a fragment between a NdeI and a SacI site. This construct allowed the cloning of just the *B. cereus* 5/B/6 β-lactamase structural gene sequence into the *E. coli* expression vector pRE2 (Reddy et al., 1989). This recombinant plasmid pRE2 was chosen because a gene cloned into the unique NdeI and SacI restriction endonuclease sites within its polymer region is correctly oriented and under the control of its strong $P_L$ promoter. The resulting plasmid is denoted as pRE2/bla. In the *E. coli* MZ-1, the temperature sensitive cI repressor binds to the $P_L$ promoter and prevents the expression of the *B. cereus* 5/B/6 β-lactamase gene on plasmid pRE2/bla at low temperatures. The cI protein is denatured at higher temperatures allowing the expression of *B. cereus* 5/B/6 β-lactamases at high levels (Nagai and Thogersen, 1984; Zuber et al., 1987). Subsequent purification of wild type and mutant *B. cereus* 5/B/6 β-lactamases resulted in a high yield of the metallo-β-lactamase that is identical to that purified from *B. cereus* 5/B/6 (Myers and Shaw, 1989; Shaw et al., 1991).

The invention described herein has utilized the method of Systematic Evolution of Ligands by Exponential Enrichment ("SELEX") to develop nucleic acid ligands for a lactamase enzyme. The nucleic acid ligands can be utilized as metallo-β-lactamase inhibitors.

DESCRIPTION OF FIGURES

FIG. 14 shows a comparison of the initial random ssDNA with the ssDNA after SELEX on a native gel. The first lane contained initial random ssDNA. The second lane contained the molecular size markers. The first marker from the bottom represents 20 bps. The fourth, fifth, sixth and seventh lanes contained PCR products after the eight round of SELEX A 12% (w/v) polyacrylamide gel (29:1 mono:bis) was used in TA buffer.

FIG. 26 shows a time-dependence of inactivation of *B. cereus* 5/B/6 metallo-β-lactamase activity by the 30-mer. The concentration of the 30-mer was 0.5 nM. Incubation and assay buffer was 50 mM MOPS, pH=7.0. cephalosporin C was used as substrate. Open circle: [I]=0 nM; filled circle: [I]=0.5 mM. I=the 30-mer.

FIG. 27 shows effect of various concentrations of the 30-mer on *B. cereus* 569/H/9 β-lactamase I activity. The enzyme was preincubated with/without the inhibitor in the buffer (50 mM MOPS, pH=7.0) for the 15 min. at 30° C. The concentration of the substrate (benzylpenicillin) was 1.1 mM.

FIG. 28 shows inhibition of bovine carboxypeptidase A by various concentrations of the 30-mer. The enzyme was preincubated with/without the inhibitor in the buffer (0.05 M TrisHCl, pH=7.5 with 0.5 M sodium chloride) for the 15 min. at 25° C. The concentration of the substrate (hippuryl-L-phenylalanine) was 1 mM.

FIG. 29 shows a secondary structure of the 30-mer predicted by the MFold program (Zuker, 1989).

FIG. 30 shows another (higher energy) secondary structure of the 30-mer predicted by the MFold program (Zuker, 1989).

FIG. 31 shows a secondary structure of the 61-mer predicted by the MFold program (Zuker, 1989).

FIG. 32 shows a secondary structure of the 10-mer predicted by the MFold program (Zuker, 1989).

FIG. 33 shows a determination of $IC_{50}$ for *B. cereus* 5/B/6 metallo-β-lactamase by the 10-mer. The enzyme was preincubated with/without the inhibitor in the buffer (50 mM MOPS, pH=7.0) for the 15 min. at 30° C. The concentration of the substrate (cephalosporin C) was 4 mM.

FIG. 34 shows a Lineweaver-Burk plot of inhibition of *B. cereus* 5/B/6 metallo-β-lactamase by the 10-mer. Filled circle: [I]=0 nM; open circle: [I]=1 nM; filled square: [I]=2 nM; open square: [I]=3 nM. I=the 10-mer.

FIG. 35 shows a slope replot to estimate $K_i$ for the 10-mer. Slope values ($K_m/V_{max}$) for each inhibitor concentration from experimental data of FIG. 34 were determined using a non-linear regression computer program (EnzymeKinetics, v. 1.2, Trinity Software). Slope values were then plotted vs. corresponding inhibitor concentrations. The x-intercept in this plot is $-K_i$.

FIG. 36 shows a intercept replot to estimate $K_i'$ for the 10-mer. Intercept values ($1/V_{max}$) for each inhibitor concentration from experimental data of FIG. 34 were determined using a non-linear regression computer program (EnzymeKinetics, v. 1.2, Trinity Software). Intercept values were then plotted vs. corresponding inhibitor concentrations. The x-intercept in this plot is $-K_i'$.

FIG. 37 shows a time-dependence of inactivation of *B. cereus* 5/B/6 metallo-β-lactamase activity by the 10-mer. The concentration of the 30-mer was 0.5 nM. Incubation and assay buffer was 50 mM MOPS, pH=7.0. cephalosporin C was used as substrate. Open circle: [I]=0 nM; filled circle: [I]=0.5 nM. I=the 10-mer.

FIG. 38 shows effect of various concentrations of the 10-mer on *B. cereus* 569/H/9 β-lactamase I activity. The enzyme was preincubated with/without the inhibitor in the buffer (50 mM MOPS, pH=7.0) for the 15 min. at 30° C. The concentration of the substrate (benzylpenicillin) was 1.1 mM.

FIG. 39 shows the effect of various concentrations of the 10-mer on bovine carboxypeptidase A. The enzyme was preincubated with/without the inhibitor in the buffer (0.05 M TrisHCl, pH=7.5 with 0.5 M sodium chloride) for the 15 min. at 25° C. The concentration of the substrate (hippuryl-L-phenylalanine) was 1 mM.

FIG. 40 shows inhibition of for *B. cereus* 5/B/6 metallo-β-lactamase by various concentrations of the 18-mer. The enzyme was preincubated with/without the inhibitor in the buffer (50 nM MOPS, pH=7.0) for the 15 min. at 30° C. The concentration of the substrate (cephalosporin C) was 4 mM.

FIG. 41 shows a determination of IQ, for *B. cereus* 5/B/6 metallo-β-lactamase in the presence of $Zn^{2+}$ ions by the 10-mer. The enzyme was preincubated with/without the inhibitor in the buffer (50 mM MOPS and 1 $ZnSO_4$, pH=7.0) for the 15 min. at 30° C. The concentration of the substrate (cephalosporin C) was 4 mM.

SUMMARY

One aspect of the current invention is a method for identifying a high affinity nucleic acid ligand to inhibit the activity of a lactamase enzyme. The method comprises several steps that initially involve preparing a candidate mixture of nucleic acids. The candidate mixture of nucleic acids is then allowed to make contact with the lactamase enzyme under controlled conditions of temperature, ionic strength and pH; the combination forms a candidate-enzyme mixture. Not all candidates bind tightly to the enzyme. The target nucleic acids may be easily partitioned from the remainder of the candidate mixture. Partitioning the target-nucleic acids from the remainder of the candidate mixture can be performed by many methods known to one skilled in the art. Once the target nucleic acids have been partitioned, they can be amplified to yield a pool of nucleic acids enriched with target nucleic acid sequences. The enriched pool of target nucleic acids have a relatively higher affinity and specificity for binding to the lactamase, whereby nucleic acid ligand of the lactamase may be identified through methods known to one skilled in the art of molecular biology (e.g. DNA sequencing).

Another aspect of the current invention involve nucleic acid ligands that inhibit an activity of lactamase. In a preferred embodiment, the lactamase is a class B, metallo-β-lactamase. Another preferred embodiment includes a specific nucleic acid ligands that inhibit *B. cereus* 5/B/6 metallo-β-lactamase. Yet another preferred embodiment includes a specific nucleic acid ligands that inhibit *B. cereus* 569/H/9 metallo-β-lactamase.

DETAILED DESCRIPTION OF PREFERRED EMBODIMENTS

Terms:

"Nucleic Acid Ligand" as used herein is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action has specific binding affinity for a target molecule, such target molecule being a three dimensional chemical structure other than a polynucleotide that binds to the nucleic acid ligand, wherein the nucleic acid ligand is not a nucleic acid having the known physiological function of being bound by the target molecule. The target molecule in a preferred embodiment of this invention is a lactamase. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mire; b) partitioning the increased affinity nucleic acids from the remainder of the candidate mixture; and c) amplifying the increased affinity nucleic acids to yield a ligand-enriched mixture of nucleic acids.

Figure 1:
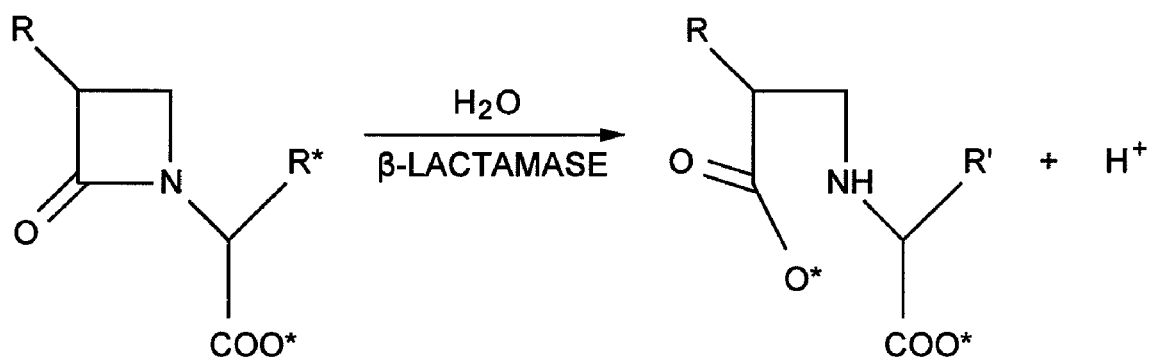
FIG. 1 shows the catalysis of hydrolysis of a generic β-lactam by a β-lactamases.
Figure 2:
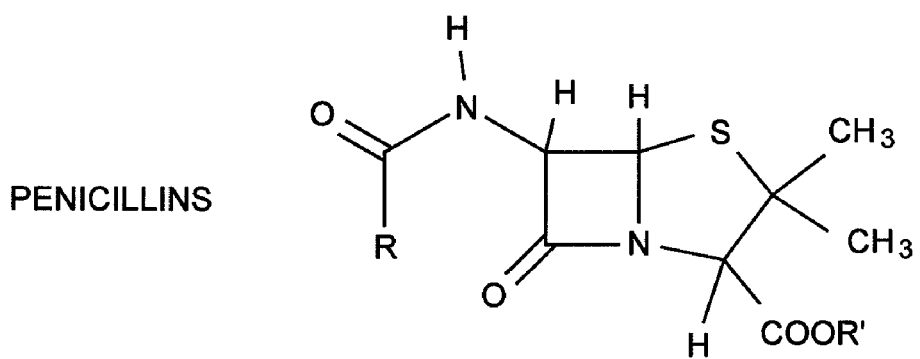
FIG. 2 shows the general structures of penicillins and cephalosporins.
Figure 2:
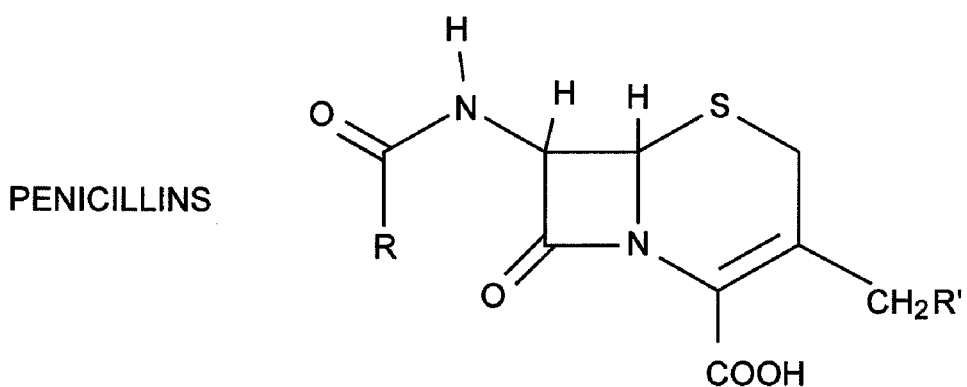
Figure 3:
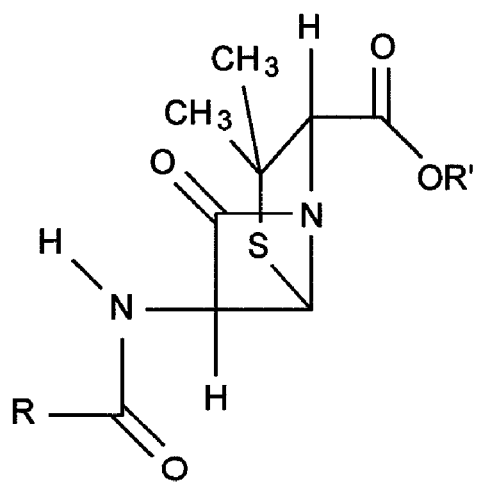
FIG. 3 shows the comparison of the structure of penicillins with the structure of D-alanyl-D-alanine-peptidoglycan.
Figure 3:
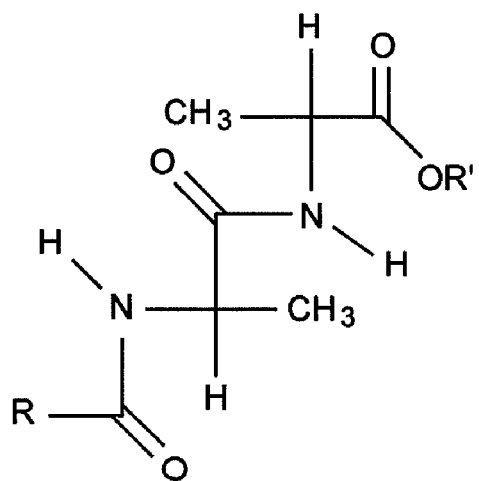

"Candidate Mixture" is a mixture of nucleic acids of differing sequence from which to select a desired ligand. The source of a candidate mixture can be from naturally occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Nucleic Acid" means either DNA, RNA, single-stranded or double-stranded and any chemical modifications thereof. Modifications include, but are not limited to, those that provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands that interact with a target in a desirable manner, for example binding to a protein, with amplification of those selected nucleic acids. Iterative cycling of the selection/amplification steps allows selection of one or a small number of nucleic acids that interact most strongly with the target from a pool that contains a very large number of nucleic acids. Cycling of the selection/amplification procedure is continued until a selected goal is achieved. In the present invention, the SELEX methodology is employed to obtain nucleic acid ligands to a lactamase enzyme.

"Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the target is a lactamase. In a preferred embodiment the lactamase is a class B metallo-lactamase.

A "labile ligand" as used herein means a nucleic acid ligand identified by the SELEX process that has a greatly decreased affinity for its target based on an adjustment of an environmental parameter. In the preferred embodiment, the environmental parameter is temperature, and the affinity of a ligand to its target is decreased at elevated temperatures.

One aspect of the current invention is a method for identifying a high affinity nucleic acid ligand to inhibit the activity of a lactamase enzyme. The method comprises several steps that initially involve preparing a candidate mixture of nucleic acids. The candidate mixture of nucleic acids is then allowed to make contact with the lactamase enzyme under controlled conditions of temperature, ionic strength and pH; the combination forms a candidate-enzyme mixture. Not all candidates bind tightly to the enzyme. The target nucleic acids may be easily partitioned from the remainder of the candidate mixture. Partitioning the target-nucleic acids from the remainder of the candidate mixture can be performed by many methods known to one skilled in the art. Once the target nucleic acids have been partitioned, they can be amplified to yield a pool of nucleic acids enriched with target nucleic acid sequences. The enriched pool of target nucleic acids have a relatively higher affinity and specificity for binding to the lactamase, whereby nucleic acid ligand of the lactamase may be identified through methods known to one skilled in the art of molecular biology (e.g. DNA sequencing).

Another aspect of the current invention involve nucleic acid ligands that inhibit an activity of lactamase. In a preferred embodiment, the lactamase is a class B, metallo-β-lactamase. In another preferred embodiment, the class B lactamase includes a *B anthracis* metallo-β-lactamase. Another preferred embodiment includes a specific nucleic acid ligands that inhibit *B. cereus* 5/B/6 metallo-β-lactamase. Yet another preferred embodiment includes a specific nucleic acid ligands that inhibit *B. cereus* 5/H/9 metallo-β-lactamase.

Materials and Methods:

Metallo-β-lactamase. The metallo-β-lactamase from *B. cereus* 5/B/6 was produced from *E. coli* MZ1 carrying the pRE2/bla plasmid and purified according to the procedures described previously (Shaw et al, 1991). The purity was ascertained by specific activity, native and SDS PAGE, and DE-MALDI-TOF. T4 DNA ligase was purchased from Promega. Restriction endonucleases NdeI and SacI were purchased from New England Biolabs, Inc. and were used according to the manufacturer's recommendations. DNA molecular weight markers (BstNI digested pBR322 and BstEII digested λ DNA) were purchased from New England Biolabs, Inc. The QuikChange Site-directed mutagenesis kit was purchased from Stratagene. DEAE-Sephacel, Sephadex G-25 (superfine), CM-Sepharose CL 6B and various columns were purchased from Pharmacia or Bio-Rad Laboratories. The Gene Clean II Kit was purchased from BIO101. Automated DNA sequencing was done on ABI PRISM™ 310 Genetic Analyzer from Applied Biosystems Inc. Synthetic olignucleotides for SELEX were synthesized using Beckman Oligo 1000M oligonucleotide synthesizers. PCR reactions were carried out using a Perkin Elmer Certus Thermal Cycler. Pfu polymerase was purchased from Stratagene. The cell suspensions were sonicated using a Heat System Ultrasonics, Inc. model W-375 sonicator. PCI (Phenol:Choroform: Isoamyl alcohol (25:24:1) and electrophoresis grade agarose were obtained from Amresco. Bovine carboxypeptidase A and hippuryl-L-phenylalamine were purchased from Sigma. PCR 20 bp low ladder, ethidium bromide, dimethysulfoxide (DMSO), acrylamide, bisacrylamide, benzylpenicillin, cephalosporin C (potassium salt), ampicillin, cesium chloride, EDTA, ethanol, glucose, sodium hydroxide, potassium hydroxide, rubidium chloride, urea, MOPS, Tris, $ZnSO_4$ and various other inorganic salts and organic solvents of reagent grade or better were obtained from Sigma Chemical Co. Difco brand bacto-agar, casamino acids and yeast extract used to make all media and plates were obtained through Fisher Scientific.

Method for assay of the purified *B. cereus* 5/B/6 metallo-β-lactamase and *B. cereus* 568/H/9 β-lactamase I. For metallo-β-lactamase activity assays, the activities using cephalosporin C as substrate were determined as previously reported (Myers and Shaw, 1989). The activity assay procedure was essentially the same as the spectrophotometric method of Davies et al. (1974) in which the substrate absorbance at 260 nm is continuously monitored during hydrolysis. One unit of activity was defined as the amount of enzyme required to catalyze the hydrolysis of 1 μmol of substrate in one minute at 30° C. All assays were carried out near $V_{max}$ using 4.3 mM cephalosporin C (approximately 10 $K_m$) dissolved in 50 mM MOPS/1 mM $ZnSO_4$, pH=7.0. The assays were performed in a 0.1 cm pathlength quartz cuvette and the total reaction volume was maintained at 250 µL.

For β-lactamase I activity assays, Davies et al. (1974) described the method of β-lactamase I activity assays. The method was modified. The enzyme sample was incubated with 20 mM EDTA (pH=7.0) for 15 min. at room temperature prior to the assay. The enzymatic hydrolysis of 1.1 mM benzylpenicillin in 10 mM sodium citrate (pH=7.0) and 1 mM EDTA was continuously monitored at 231 nm at 30° C. One unit of β-lactamase activity was defined as the amount of enzyme required to hydrolyze one µmole of substrate/min. at 30° C. at pH=7.0. The protein concentrations were determined by the method of Lowry (Lowry et al., 1951) using bovine serum albumin as a standard. This method was used throughout for all protein determinations.

Method for reversible inhibition studies for metallo-β-lactamase. To test reversible inhibitors, the preincubation mixtures contained possible inhibitors in 50 mM MOPS buffer, pH=7.0 at 30° C. for 15 minutes. The metallo-β-lactamases were incubated with the same final concentration of the possible inhibitors as the preincubation mixture in 50 mM MOPS buffer (pH=7.0) for 15 minutes. The enzyme activity remaining was determined (Myers and Shaw, 1989).

Method for SELEX Oligonucleotides. In 1990, the laboratories of G. F. Joyce (La Jolla), J. W. Szostak (Boston), and L. Gold (boulder) independently developed a technique, which allows the simultaneous screening of a large number of nucleic acid, molecules for different functionalities. This method is commonly known as 'in selection' (Ellington and Szostak, 1990), 'in vitro evolution' Joyce, 1989), or 'SELEX' (Systematic Evolution of Ligands by Exponential enrichment) (Tuerk and Gold, 1990). With the in selection technique large random pools of nucleic acids can be screened for a particular functionality, such as the binding to small organic molecules (Famulk, 1994), large proteins (Tuerk and Gold, 1990; Chen and Gold, 1994) or the alteration or de now generation of ribozyme catalysis (Robertson and Joyce, 1990; Bartel and Szonstale, 1993). Functional molecules ('aptamera' from 'aptus'; lat.=to fit) are selected from the mainly non-functional pool of RNA or DNA by column chromatography or other selection techniques that are suitable for the enrichment of any desired property.

Figure 4:
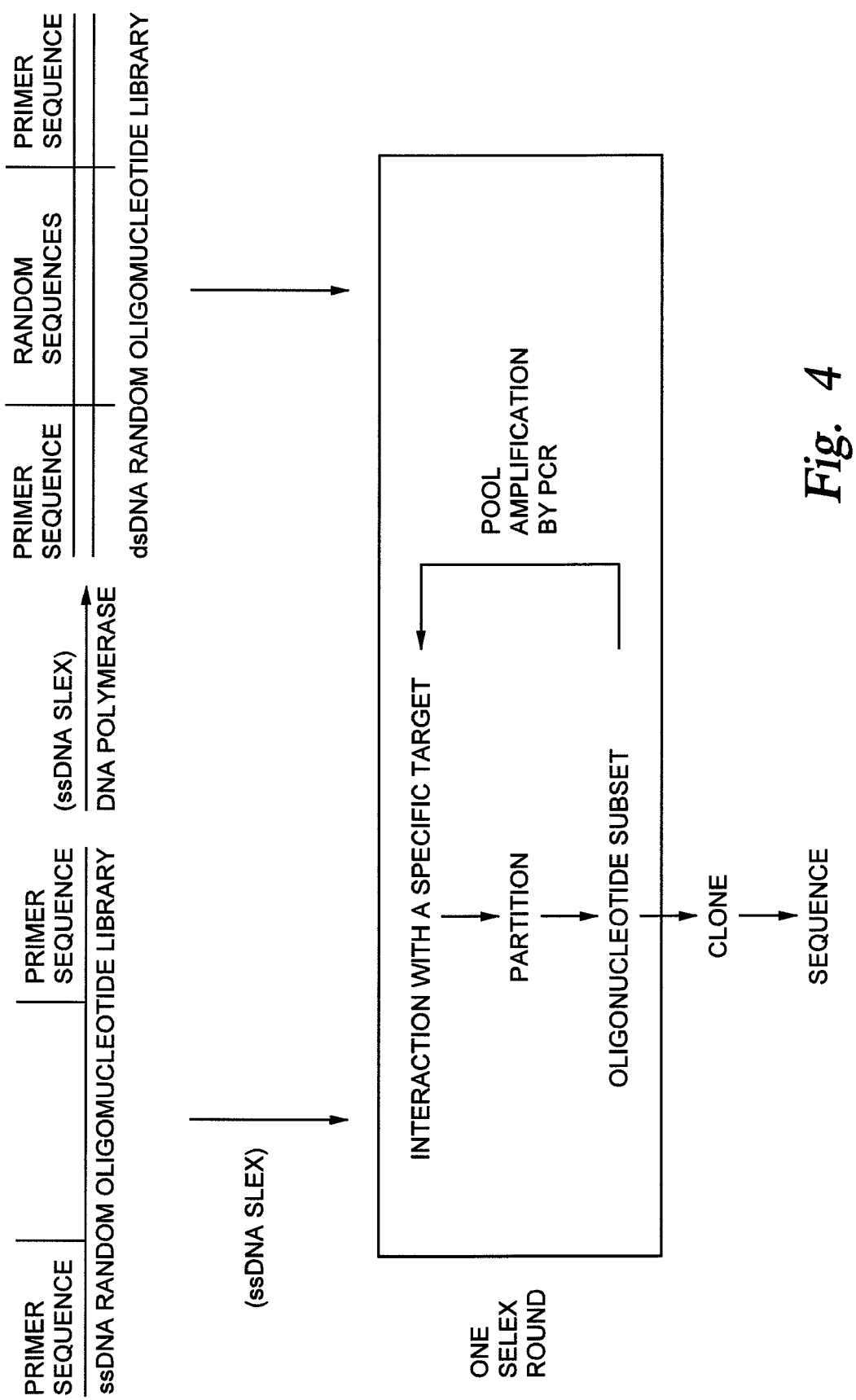
FIG. 4 shows a diagrammatic representation of the SELEX procedure that was modified from Gold et al., 1995.
Figure 5:
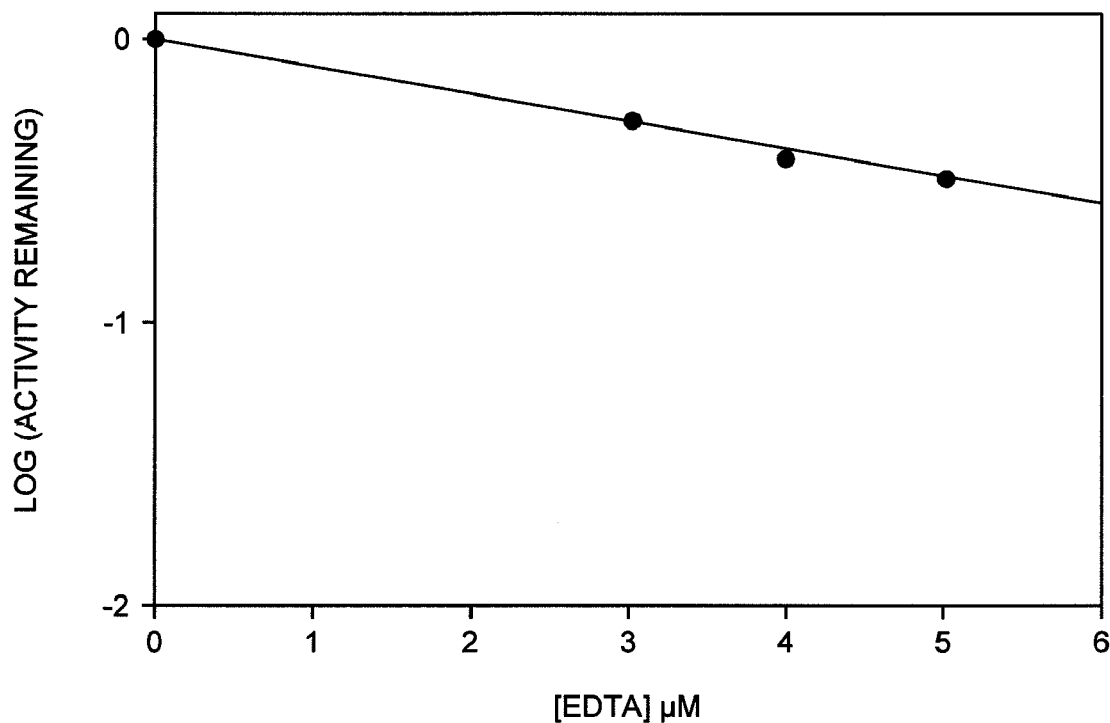
FIG. 5 shows a determination of $IC_{50}$ for *B. cereus* 5/B/6 metallo-β-lactamase by EDTA. The enzyme was preincubated with/without EDTA in the buffer (50 mM MOPS, pH=7.0) for 15 min. at 30° C. The concentration of the substrate (cephalosporin C) was 4 mM.

The method is conceptually straightforward: a starting, degenerate oligonucleotide pool is generated using a standard DNA-oligonucleotide synthesizer. The instrument synthesizes an oligonucleotide with a completely random base-sequence, which is flanked by defined primer binding sites. The immense complexity of the generated pool justifies the assumption that it may contain a few molecules with the correct secondary and/or tertiary structures that bind tightly and specifically to a target enzyme and inhibit the enzymatic activity. These are selected, for example, by affinity chromatography or filter binding. Because a pool of such high complexity can be expected to contain only a very small fraction of functional molecules, several purification steps are usually required. Therefore, the very rare "active" molecules are amplified by the polymerase chain reaction ("PCR"). In this way, iterative cycles of selection can be carried out. Successive selection and amplification cycles result in an exponential increase in the abundance of functional sequences, until they dominate the population. A generalized diagram of the SELEX protocol is shown in FIG. 4, which shows a diagrammatic representation of the SELEX procedure (modified from Gold et al., 1995). The primer sequences permit amplification, and in its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

U.S. Pat. No. 5,637,459 entitled "Systematic Evolution of Ligands by Exponential Enrichment Chimeric Selex" issued on Jun. 30, 1998 with Burke et al., listed as inventors, and U.S. Pat. No. 5,773,598 entitled "Systematic Evolution of Ligands by Exponential Enrichment: Chimeric Selex" issued on Jun. 30, 1998 with Burke et al., listed as inventors, both of these patents describe and elaborate on the SELEX process in great detail. Both cited patents are herein incorporated by reference. Included are targets that can be used in the process; methods for partitioning nucleic acids within a candidate mixture; and methods for amplifying partitioned nucleic acids to generate enriched candidate mixture. The SELEX Patents also describe ligands obtained to a number of target species, including both protein targets where the protein is and is not a nucleic acid binding protein.

The SELEX process provides high affinity ligands of a target molecule. Oligonucleotides were produced using a Beckman Instruments, Inc. OLIGO 1000M DNA synthesizer. One 61 base single-stranded DNA was synthesized containing 30 bases of randomized sequence ("30N") between two primer regions encompassing SacI and NdeI recognition sites. This template DNA was then amplified by PCR with the corresponding primers SeqID# 1 that is a 5' Primer (16-mer) with a NdeI restriction site (e.g. 5'GCGC CATATGCGCGCG3') and SeqID# 2 that is a 3' Primer (15-mer) with a SacI restriction site (e.g. 5'CGC GAGCTCCGCGCG3').

For this invention, a pool of $4^{30}=1.2\times10^{18}$ 61-mer oligonucleotides were synthesized to have 15 and 16 nucleotides to serve as polymerase chain reaction ("PCR") primers at their 5' and 3' termini respectively, and also contain an internal 30-nucleotide completely random sequence. Single-stranded DNA has been selected that not only binds tightly and specifically to the *B. cereus* 5/B/6 metallo-β-lactamase, but also is able to inhibit this enzyme.

Prediction of secondary structure of aptamers. The MFold program is an adaptation of the mfold package (version 2.3) by Zuker (1989) and Jaeger et al. (1989, 1990) that has been modified to work with the Wisconsin Packages™. Their method uses the energy rules developed by Turner et al. (1988) to predict optimal secondary structures for a RNA molecule and the energy rules compiled and developed by Allawi and SantaLucia (1997) to predict optimal and suboptimal secondary structures for a single-stranded DNA molecule. This approach will provide a first-approximation prediction of secondary structure from sequence.

Gel shift assay. The electrophoretic mobility shift assay used 6% (w/v) polyacrylamide gels (29:1 mono:bis) in 20 mM Tris-acetate HA) buffer (pH=7.0), polymerized with 0.07% (w/v) ammonium persulfate and 0.028% (v/v) TEMED. The stock enzyme in 150 mM ammonium sulfate, 10 mM sodium citrate (pH=7.0), 1 mM $ZnSO_4$, and 30% (v/v) glycerol, was heated for 30 min at 60° C. to denature any possible other proteins. This enzyme is stable at 60° C. The enzyme was centrifuged and the supernatant was collected. The enzyme was diluted with dilution buffer (20 mM TA and 1 mM $ZnSO_4$, pH=7.0). The synthesized library of 61-mer ssDNA described above was used for SELEX selection. The ssDNA was incubated with the enzyme at 30° C. for 15 min in TA buffer with an appropriate concentration of NaCl. The total reaction volume was 20 μL. The amounts of the ssDNA, enzyme and NaCl in the incubated buffer were adjusted (Table 1). After 15 min, 40% (v/v) glycerol was added to samples to give 10% (v/v) glycerol as a final concentration. Samples were run in the 6% (w/v) polyacrylamide gel at 200 V for 25 to 30 minutes. From the seventeenth round to the twenty-first round, the time period of the incubation of ssDNA and enzyme was 2.5 hours.

TABLE 1

Salt concentration conditions of SELEX.

| Round | ssDNA | Enzyme | NaCl |
|---|---|---|---|
| 1 | 3 μM | 20 μM | 10 mM |
| 2 | 3 μM | 20 μM | 10 mM |
| 3 | 1.5 μM | 20 μM | 10 mM |
| 4 | 1.5 μM | 10 μM | 10 mM |
| 5 | 1.5 μM | 10 μM | 10 mM |
| 6 | 1.5 μM | 5 μM | 10 mM |
| 7 | 1.5 μM | 5 μM | 10 mM |
| 8 | 1.5 μM | 2 μM | 10 mM |
| 9 | 1.5 μM | 1.5 μM | 10 mM |
| 10 | 1.5 μM | 1.5 μM | 10 mM |
| 11 | 1.5 μM | 1.5 μM | 10 mM |
| 12 | 1.5 μM | 1.5 μM | 10 mM |
| 13 | 1.5 μM | 1.5 μM | 15 mM |
| 14 | 1.5 μM | 1.5 μM | 15 mM |
| 15 | 1.5 μM | 1.5 μM | 15 mM |
| 16 | 1.5 μM | 1.5 μM | 20 mM |
| 17 | 1.5 μM | 1.5 μM | 50 mM |
| 18 | 1.5 μM | 1.5 μM | 50 mM |
| 19 | 1.5 μM | 1.5 μM | 50 mM |
| 20 | 1.5 μM | 1.5 μM | 50 mM |
| 21 | 1.5 μM | 1.5 μM | 50 mM |

The enzyme:ssDNA complexes were separated from free DNAs on the 6% (w/v) polyacrylamide gels described above. The resulting gel was soaked in the incubation buffer with the ethidium bromide for 10 minutes and was destained in dd$H_2O$. The enzyme:ssDNA complexes were visualized by UV illumination using TM-36 Chromato-UVE transilluminater from UVP Inc. and were excised. The ssDNA was extracted by the modified crush and soak method (Maxam and Gilbert, 1977) with the following modifications: After cutting out the segment of the gel using a sharp scalpel or razor blade, the slice was transferred to a microcentrifuge tube. The slice was crushed by a disposable pipette tip. The slice was weighed to determine its volume and 1-2 volumes of elution buffer (0.5 M ammonium acetate, 1 mM EDTA (pH=8.0), and 0.1% (w/v) SDS was added. The tube was incubated at 45° C. on a rotary platform for 2.5-3 hours. After centrifuging the tube at 12,000 g for 1 minute, the supernatant was transferred to a fresh microcentrifuge tube. To avoid any fragments of polyacrylamide, a plastic column containing glass wool was used to centrifuge the supernatant. A one-half volume aliquot of elution buffer was added to the remaining pellet to be vortexed and recentrifuged. The supernatant and gel fragments were poured into the plastic column and spun for 15 seconds. 2-2.5 volumes of 100% ethanol was added to the sample from this column and placed at −20° C. for 1 hour and at −80° C. for 10-15 minutes. The tube was spun for 10-15 minutes. This ethanol precipitation step will help the removal of ethidium bromide to provide the right conformation of ssDNA. The supernatant was discarded. The pellet was washed with 70% ethanol and was dried.

Generation of single-stranded DNA by asymmetric PCR. The ssDNA was subjected to amplification with 2.5 units of the pfu polymerase. The reaction mixture, including 200 ng of 5' primer (16 mer) and 100 ng of 3'primer (15 mer), was subjected to 30 cycles of 45 seconds at 94° C., 45 seconds at 55° C. and 6 seconds at 72° C. This was followed by ten minutes at 72° C. to allow all annealed primers to finish extending. The optimal 10× buffer for PCR was 100 mM Tris-HCl (pH 8.8), 35 mM $MgCl_2$ and 250 mM KCl. The final concentration of dNTP was 2 mM. The total reaction volume was 100 μL.

The PCR products were purified from 12% (w/v) polyacrylamide gel (29:1 mono:bis). To confirm that the PCR product was ssDNA containing a 30 base insertion, the initial pool of ssDNA containing 30 random bases was compared with the PCR product on 12% (w/v) polyacrylamide (29:1 mono:bis) and 8 M urea gel in TBE buffer (Sambrook et al., 1989).

Cloning and sequencing. The plasmid pRE2/bla was digested with restriction endonucleases NdeI and SacI (Reddy, Peterkofsky and McKenney, 1989). All these double-digestion mixtures were electrophoretically separated on 1.0% (w/v) agarose gel in TBE buffer at 60 V in the absence of ethidium bromide for 3 hours. The linearized pRE2 vector and the metallo-lactamase gene fragment were then located by staining the gels in 5 μg/mL ethidium bromide solution and visualized under UV. The restricted linear pRE2 and the metallo-β-lactamase gene fragment were then excised from the gels, and the DNAs were extracted by the Gene Clean Kit (purchased from BIO 101).

The ssDNA was amplified by PCR to make dsDNA. After ethanol precipitation, the fixed regions was digested with restriction endonuclease NdeI and SacI. The digested fragment was loaded on 12% (w/v) polyacrylamide gels (29:1 mono:bis) and was then purified by the modified crush and soak method.

Ligation of the fragments with the linear pRE2 vector was accomplished with T4 DNA ligase (purchased from Promega Co.) at 4° C. overnight or at room temperature for 3 hours. For each ligation, 100 ng of linearized pRE vector, 1.11 ng of fragment and 3 units of T4 DNA ligase were mixed together in ligation buffer in a total volume of 10 µL. After incubation, the mixture was used to transform $E.\ coli$ strain TAP 56 competent cell prepared by the Hanahan method (Hanahan, 1983). Transformed cells were incubated at 30° C. for 2-5 hours and were then put into LB medium that contained 1.0% (w/v) casamino acids, 0.5% (w/v) yeast extract, 0.5% (w/v) sodium chloride (adjusted to pH=7.0 with NaOH) and 50 µg/mL ampicillin. The culture was incubated at 30° C. overnight. The subcloned plasmid DNA was prepared by the boiling miniprep method (Sambrook et al., 1989). The DNA extracted by boiling miniprep was sequenced by an ABI PRISM™ 310 Genetic Analyzer. After finding the sequence, the 30-mer insertion was synthesized by on a Beckman Instruments Inc. OLIGO 1000M DNA synthesizer. The synthesized 30-mer was purified by 12% (w/v) polyacrylamide gel for all further experiments.

Method for assay of bovine carboxypeptidase A. The assay of bovine carboxypeptidase A is based on the method of Folk and Schirmer (1963). The rate of hydrolysis of hippuryl-L-phenylalanine is determined by monitoring the increase in absorbance at 254 nm (25° C., pH=7.5). The enzyme was dissolved in 10% lithium chloride to a concentration of 1-3 units per mL. Hippuryl-L-phenylanine (0.001 M) was dissolved in 0.05 M TrisHCl, pH=7.5 with 0.5 M sodium chloride. In a 1 cm cuvette, 1.0 mL of substrate was added and incubated in the spectrophotometer at 25° C. for 3-4 minutes to reach temperature equilibration and establish blank rate. Fifty µL of diluted enzyme was added to record increase in $A_{254}$. The enzyme was preincubated with/without the inhibitor in the buffer for 15 min. at 25° C.

The invention may be better understood with reference to the following examples, which are representative of some of the embodiments of the invention, and are not intended to limit the invention.

EXAMPLE 1

Inhibition Studies

Figure 6:
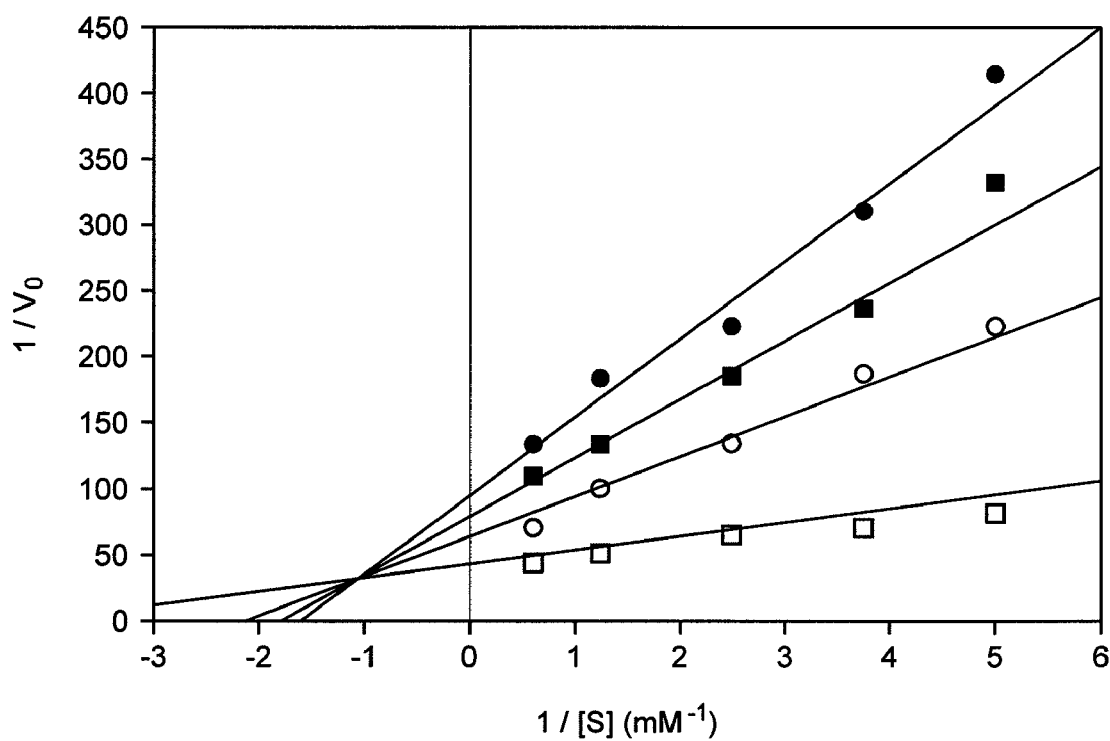
FIG. 6 shows a Lineweaver-Burk plot of inhibition of *B. cereus* 5/B/6 metallo-β-lactamase by EDTA. Open square: [I]=0 μM, open circle: [I]=3 μM; filled square: [I]=4 μM; filled diamond: [I]=5 μM. I=EDTA.

As a preliminary control study, EDTA (FIGS. 5, 6, 7 and 8) and 2-mercaptoethanol (FIGS. 9, 10, 11 and 12) were tested. The data is presented in Table 2. From the kinetic study, EDTA and 2-mercaptoethanol showed noncompetitive inhibition (FIGS. 6 and 10). The values of $K_i$ (dissociation constant for the inhibitor from the enzyme-inhibitor complex) and $K_i'$ (dissociation constant for the inhibitor from the enzyme-substrate-inhibitor complex) as determined by slope and intercept replots (FIGS. 7, 8, 11 and 12) are listed in Table 2.

The $IC_{50}$ value, that represents the concentration of inhibitor required to affect a 50% loss of activity of free enzyme, was determined by measuring the rate of enzymatic hydrolysis of cephalosporin C after the enzyme has been preincubated for 15 minutes and assayed in presence of different amounts of inhibitor. The $IC_{50}$ values of EDTA, 2-mercaptoethanlol, compounds 6 and 7 were 3.1 µM and 4.0 µM, respectively (Table 2), FIG. 5. Determination of $IC_{50}$ for $B.\ cereus$ 5/B/6 metallo-β-lactamase by EDTA. The enzyme was preincubated with/without EDTA in the buffer (50 mM MOPS, pH=7.0) for 15 min. at 30° C. The concentration of the substrate (cephalosporin C) was 4 mM.

FIG. 6. Lineweaver-Burk plot of inhibition of $B.\ cereus$ 5/B/6 metallo-β-lactamase by EDTA. Open square: [I]=0 µM; open circle: [I]=3 µM; filled square: [I]=4 µM filled diamond: [I]=5 µM I=EDTA.

Figure 7:
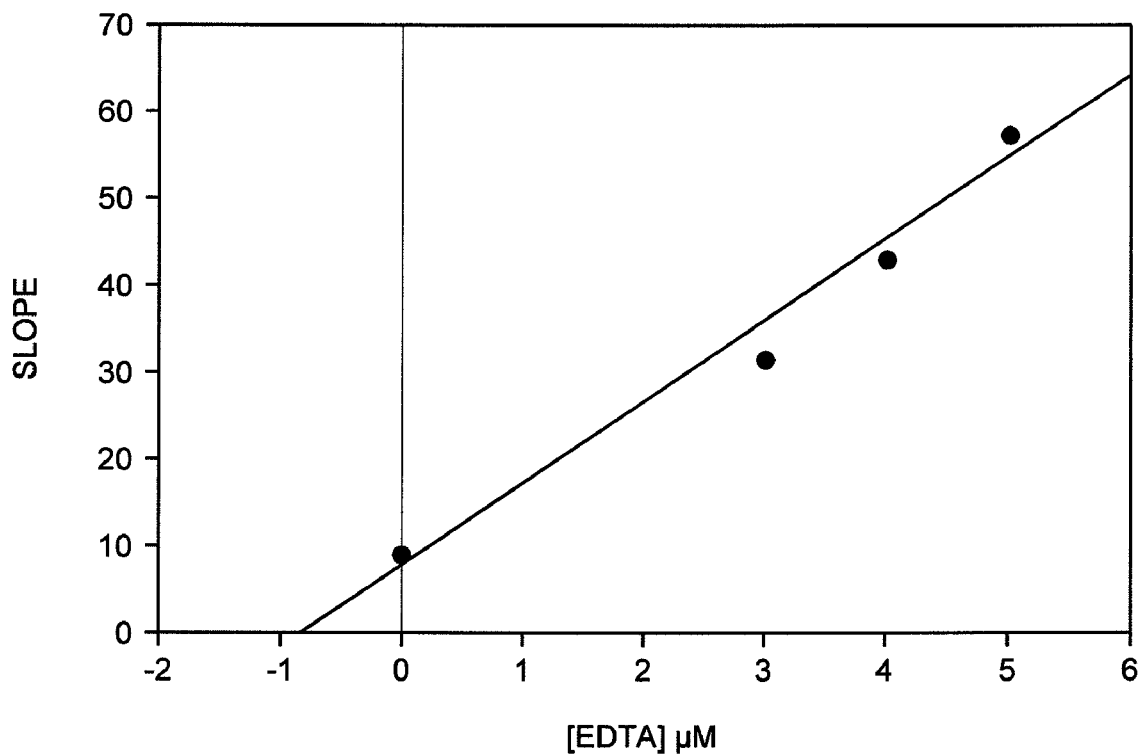
FIG. 7 shows a slope replot to estimate $K_i$ for EDTA. Slope values ($K_m/V_{max}$) for each inhibitor concentration from experimental data of FIG. 6 were determined using a non-linear regression computer program (EnzymeKinetics, v. 1.2, Trinity Software). Slope values were then plotted vs. corresponding inhibitor concentrations. The x-intercept in this plot is $-K_i$.

FIG. 7. Slope replot to estimate $K_i$ for EDTA. Slope values $(K_m/V_{max})$ for each inhibitor concentration from experimental data of FIG. 6 were determined using a non-linear regression computer program (EnzymeKinetics, v. 1.2, Trinity Software). Slope values were then plotted vs. corresponding inhibitor concentrations. The x-intercept in this plot is $-K_i$.

Figure 8:
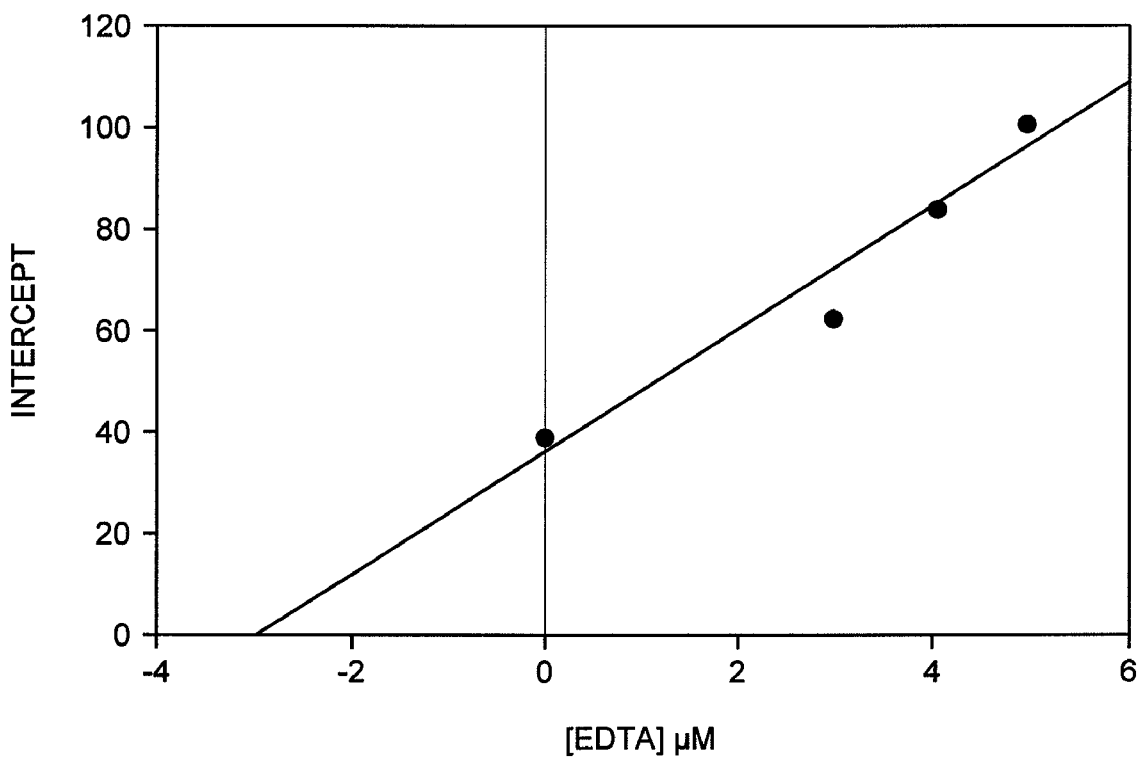
FIG. 8 shows a intercept replot to estimate $K_i'$ for EDTA. Intercept values ($1/V_{max}$) for each inhibitor concentration from experimental data of FIG. 6 were determined using a non-linear regression computer program (EnzymeKinetics, v. 1.2, Trinity Software). Intercept values were then plotted vs. corresponding inhibitor concentrations. The x-intercept in this plot is $-K_i'$.

FIG. 8. Intercept replot to estimate $K_i'$ for EDTA. Intercept values $(1/V_{max})$ for each inhibitor concentration from experimental data of FIG. 6 were determined using a non-linear regression computer program (EnzymeKinetics, v. 1.2, Trinity Software). Intercept values were then plotted vs. corresponding inhibitor concentrations. The x-intercept in this plot is $-K_i'$.

Figure 9:
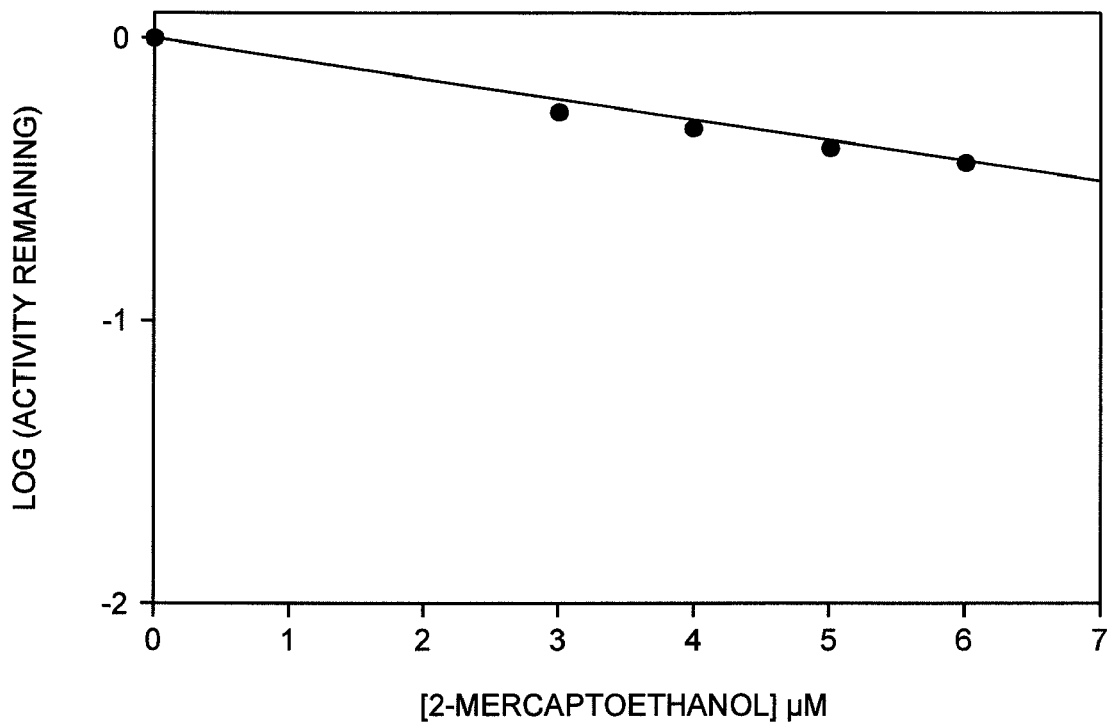
FIG. 9 shows a determination of $IC_{50}$ for B. cereus 5/B/6 metallo-β-lactamase by 2-mercaptoethanol. The enzyme was preincubated with/without 2-mercaptoethanol in the buffer (50 mM MOPS, pH=7.0) for the 15 min. at 30° C. The concentration of the substrate (cephalosporin C) was 4 mM.
Figure 10:
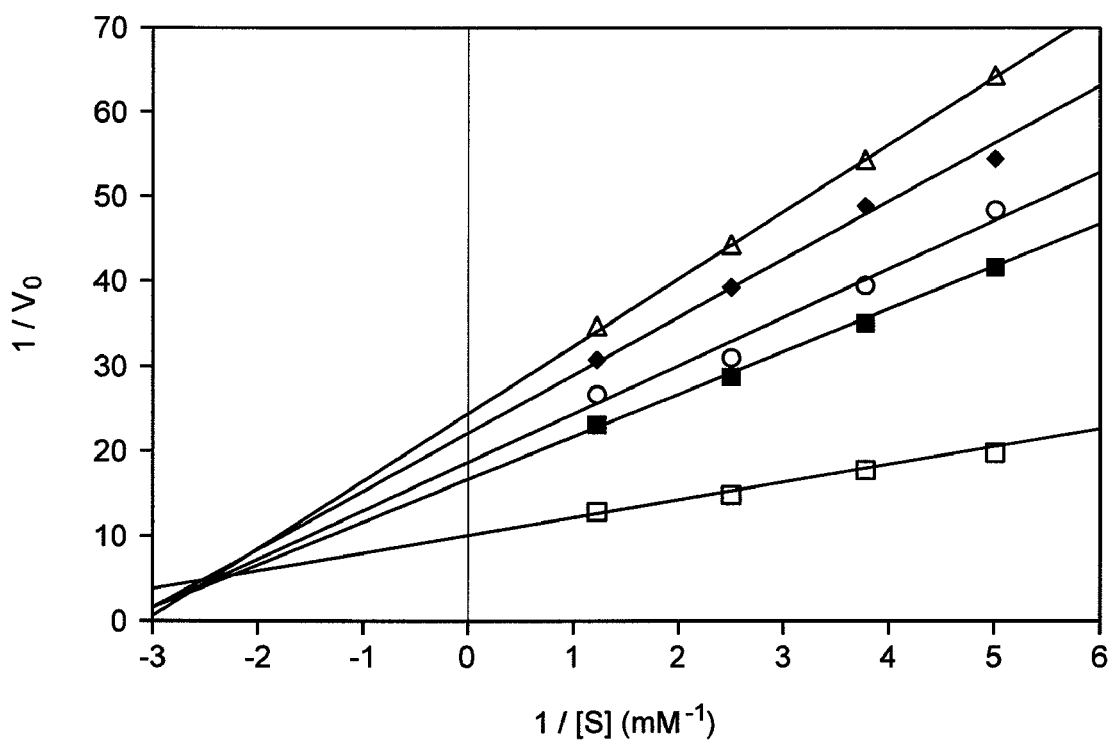
FIG. 10 shows a Lineweaver-Burk plot of inhibition of B. cereus 5/B/6 metallo-β-lactamase by 2-mercaptoethanol. Open square: [I]=0 μM; filled square: [I]=3 μM; open circle: [I]=4 μM; filled diamond: [I]=5 μM; open triangle: I=6 μM. I=2-mercaptoethanol.

FIG. 9. Determination of $IC_{50}$ for $B.\ cereus$ 5/B/6 metallo-β-lactamase by 2-mercaptoethanol. The enzyme was preincubated with/without 2-mercaptoethanol in the buffer (50 mM MOPS, pH=7.0) for the 15 min. at 30° C. The concentration of the substrate (cephalosporin C) was 4 MA.

FIG. 10. Lineweaver-Burk plot of inhibition of $B.\ cereus$ 5/B/6 metallo-β-lactamase by 2-mercaptoethanol. Open square: [I]=0 µM; filled square: [I]=3 µM; open circle: [I]=4 µM; filled diamond: [I]=5 µM; open triangle: I=6 µM. I=2-mercaptoethanol.

Figure 11:
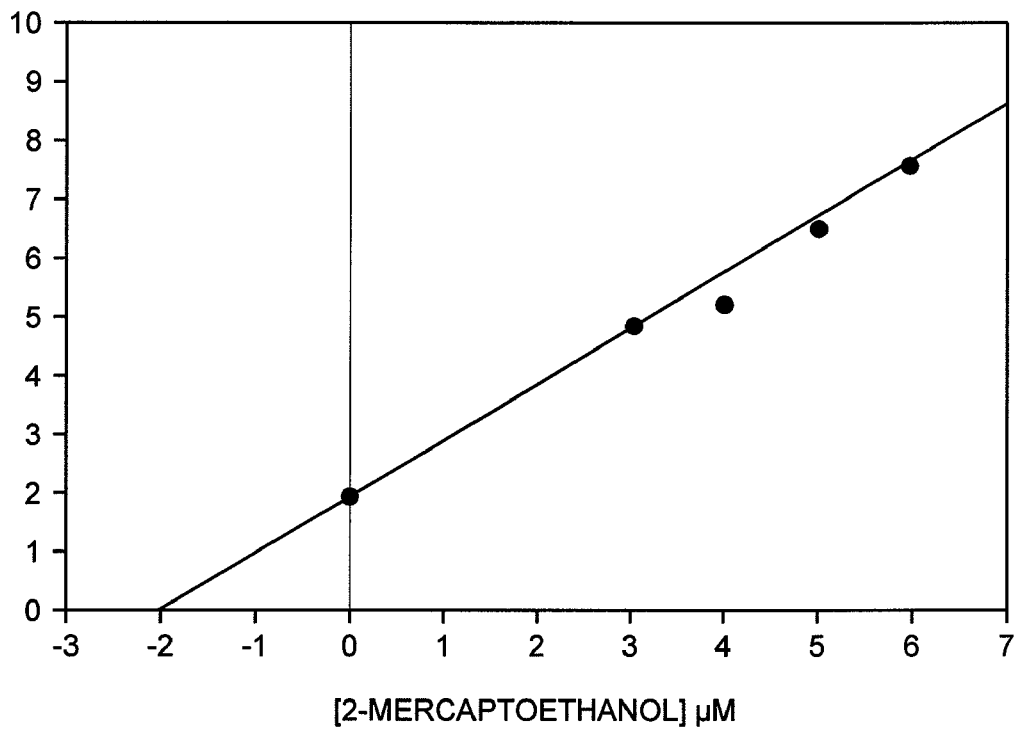
FIG. 11 shows a slope replot to estimate $K_i$ for 2-mercaptoethanol. Slope values ($K_m/V_{max}$) for each inhibitor concentration from experimental data of FIG. 10 were determined using a non-linear regression computer program (EnzymeKinetics, v. 1.2, Trinity Software). Slope values were then plotted vs. corresponding inhibitor concentrations. The x-intercept in this plot is $-K_i$.

FIG. 11. Slope replot to estimate K; for 2-mercaptoethanol. Slope values $(K_m/V_{max})$ for each inhibitor concentration from experimental data of FIG. 10 were determined using a non-linear regression computer program (EnzymeKinetics, v. 1.2, Trinity Software). Slope values were then plotted vs. corresponding inhibitor concentrations. The x-intercept in this plot is $-K_i$.

Figure 12:
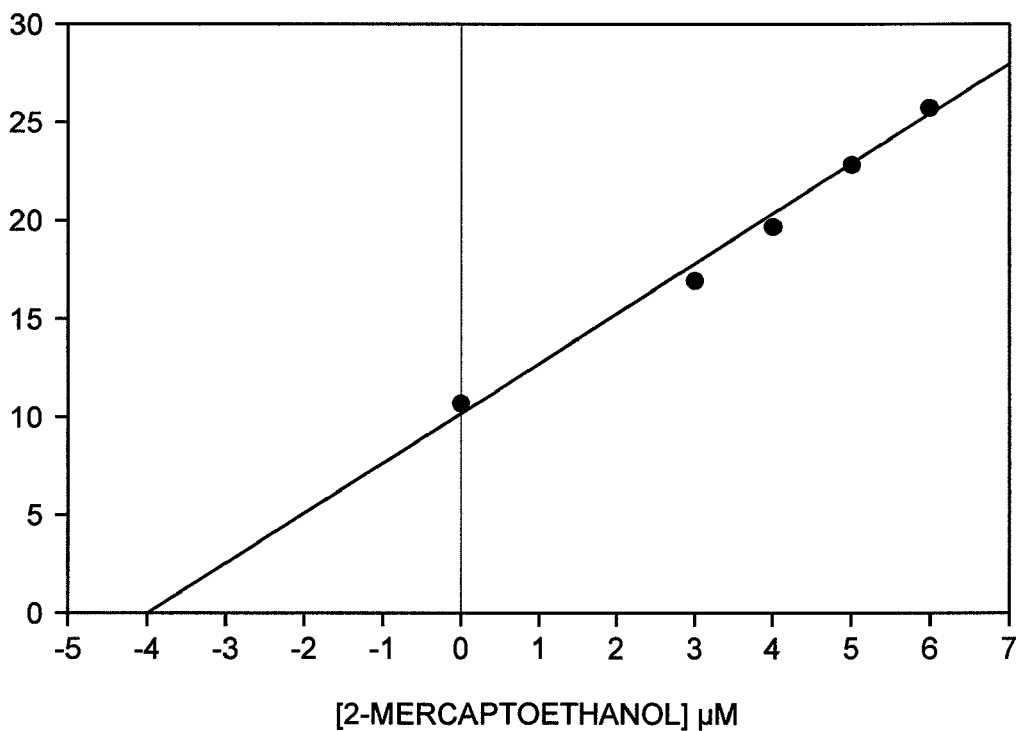
FIG. 12 shows a intercept replot to estimate $K_i'$ for 2-mercaptoethanol. Intercept values ($1/V_{max}$) for each inhibitor concentration from experimental data of FIG. 10 were determined using a non-linear regression computer program (EnzymeKinetics, v. 1.2, Trinity Software). Intercept values were then plotted vs. corresponding inhibitor concentrations. The x-intercept in this plot is $-K_i'$.

FIG. 12. Intercept replot to estimate $K_i'$ for 2-mercaptoethanol. Intercept values $(1/V_{max})$, for each inhibitor concentration from experimental data of FIG. 10 were determined using a non-linear regression computer program (EnzymeKinetics, v. 1.2, Trinity Software). Intercept values were then plotted vs. corresponding inhibitor concentrations. The x-intercept in this plot is $-K_i'$.

TABLE 2

Reversible inhibition of $B.\ cereus$ 5/B/6 metallo-β-lactamase.

| | $IC_{50}$ | $K_i$ | $K_i'$ |
| --- | --- | --- | --- |
| EDTA | 3.1 µM | 0.75 µM | 2.9 µM |
| 2-mercaptoethanol | 4.0 µM | 2.0 µM | 4.0 µM |

EXAMPLE 2

Combinatorial Approach to Inhibition of Metallo-β-lactamases: Selex

A pool of $4^{30}$ ($1.2 \times 10^{18}$) 61-mer oligonucleotides, that share 15 and 16 nucleotide sites for polymerase chain reaction (PCR) primers at their 5' and 3' termini respectively and also contain an internal random sequence 30-nucleotide was synthesized.

After incubating the enzyme with the pool of 61-mer oligonucleotides, the enzyme:ssDNA complex was separated from free ssDNA by electrophoresis.

Figure 13:
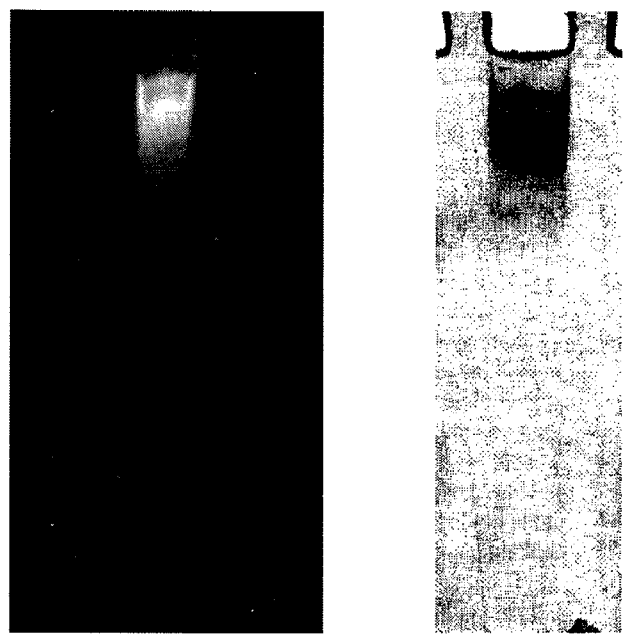
FIG. 13 shows the existence of a nucleic acid:protein complex. On the left, the gel was stained by ethidium bromide. On the right, the gel was stained with Coomassie Brilliant Blue R250. The bound ssDNA can be recognized by ethidium bromide fluorescence and the protein can be identified by Coomassie Brilliant Blue R250. In this experiment, 20 μM enzyme and 1.5 μM ssDNA were used to make the complex. The buffer used for incubation was 20 mM TA (20 mM Tris/20 mM acetate) (pH=7.0) and 1 mM $ZnSO_4$. The B. cereus 5/B/6 metallo-β-lactamase is a cationic enzyme. If there were no ssDNA binding to the enzyme, the enzyme would not migrate into the gel but would rather travel up the gel toward the cathode and out of the sample well area. The bound ssDNA provides negative charges for migration down the gel toward the anode.

FIG. 13 shows the existence of a nucleic acid:protein complex and was obtained by staining in ethidium bromide and Coomassie Brilliant Blue R250. The *B. cereus* 5/B/6 metallo-β-lactamase is a cationic enzyme. If there were no ssDNA binding to the enzyme, the enzyme would not migrate into the gel but would rather travel up the gel toward the cathode and out of the sample well area. The bound ssDNA provides negative charges for migration down the gel toward the anode. The bound ssDNA can be recognized by ethidium bromide fluorescence and the protein can be identified by Coomassie Brilliant Blue R250.

Figure 14:
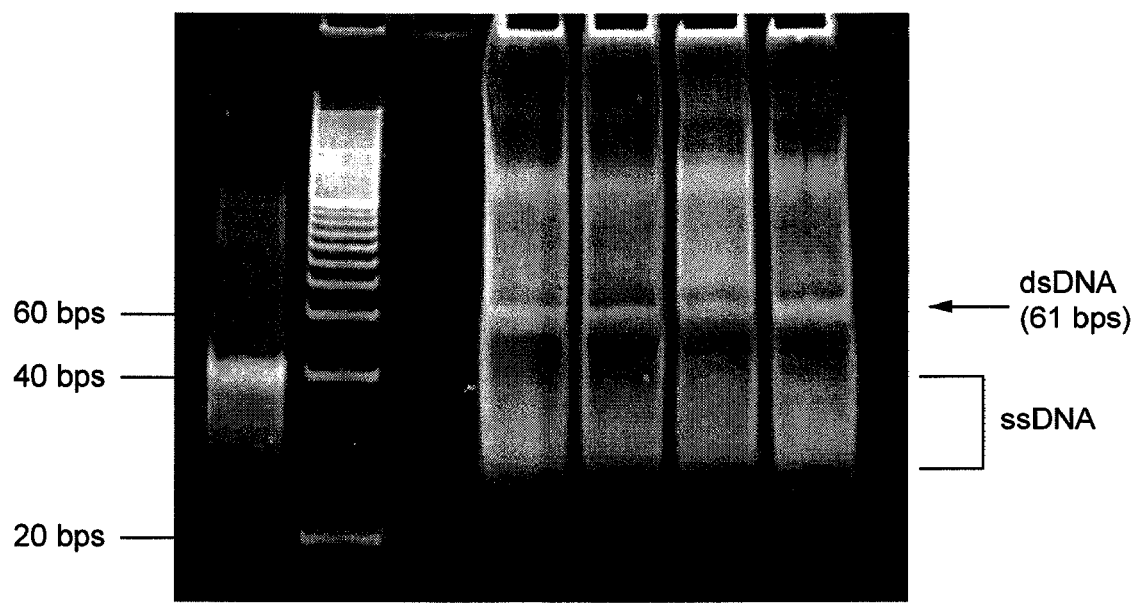
In FIG. 14 shows PCR products from SELEX migrated differently compared from the initial random ssDNA. This difference of migration and the broad nature of band of the PCR products can be due to the variety of possible secondary and tertiary structures of the PCR products.

In FIG. 14, the PCR products from SELEX migrated differently compared from the initial random ssDNA. This difference of migration and the broad nature of band of the PCR products can be due to the variety of possible secondary and tertiary structures of the PCR products.

Figure 15:
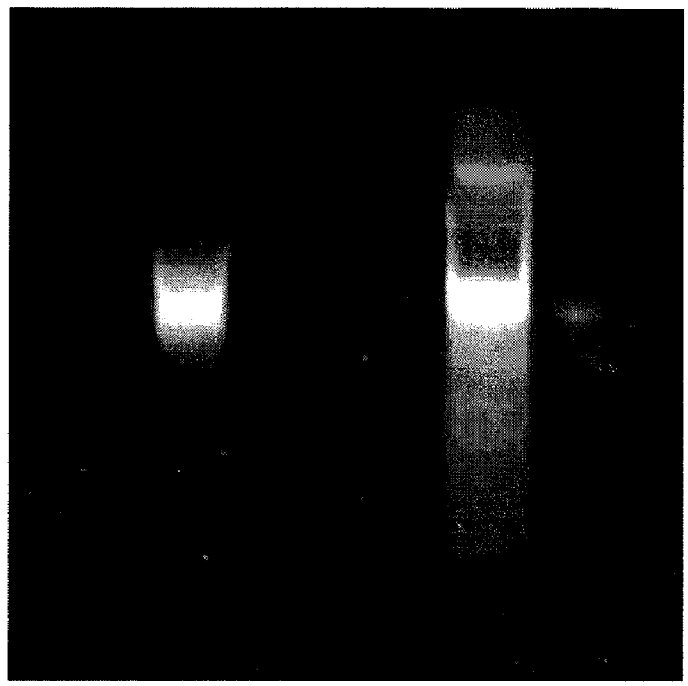
FIG. 15 shows a comparison of the initial random ssDNA with the ssDNA after SELEX on a denaturing gel. The left lane contained ssDNA after SELEX and the right lane contained initial random ssDNA. The 12% polyacrylamide gel (29:1 mono:bis) was run with 8M urea in TBE buffer (45 mM Tris, 45 mM boric acid and 1 mM EDTA, pH=8.0).

To confirm that the excised band from the PCR products contained the sought-for ssDNA, the initial random ssDNA was compared with the ssDNA generated by PCR after SELEX on an 8 M urea gel FIG. 15). The results of the comparison showed that the electrophoretic migration of the ssDNA after SELEX was essentially identical to that of the initial random ssDNA.

Figure 18:
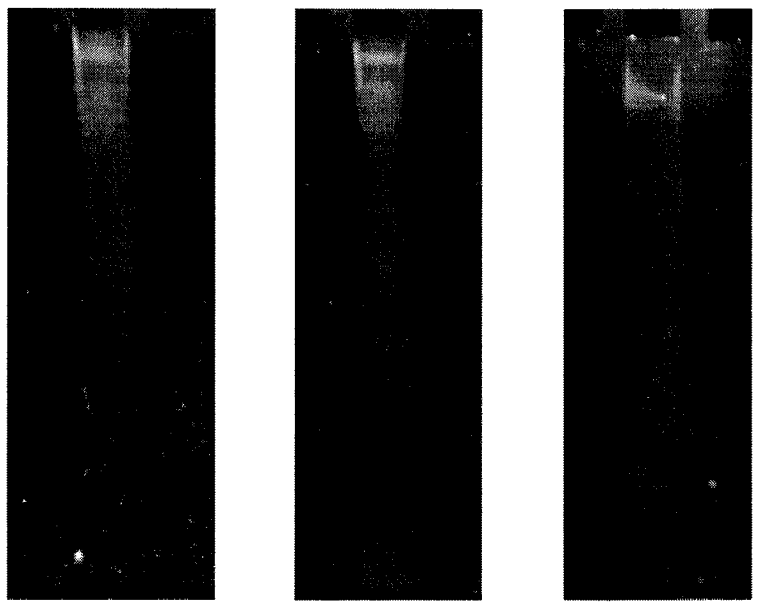
FIG. 18 shows the middle rounds of SELEX. The first, second, third lanes are for the sixth, seventh, eighth round SELEX, respectively. The gel shift assays were carried out as described in Methods. The sixth round contained 5 μM enzyme, 1.5 μM ssDNA and 10 mM NaCl. The seventh round contained 5 μM enzyme, 1.5 μM ssDNA and 10 mM NaCl. The eighth round contained 2 μM enzyme, 1.5 μM-ssDNA and 10 mM NaCl.
Figure 20:
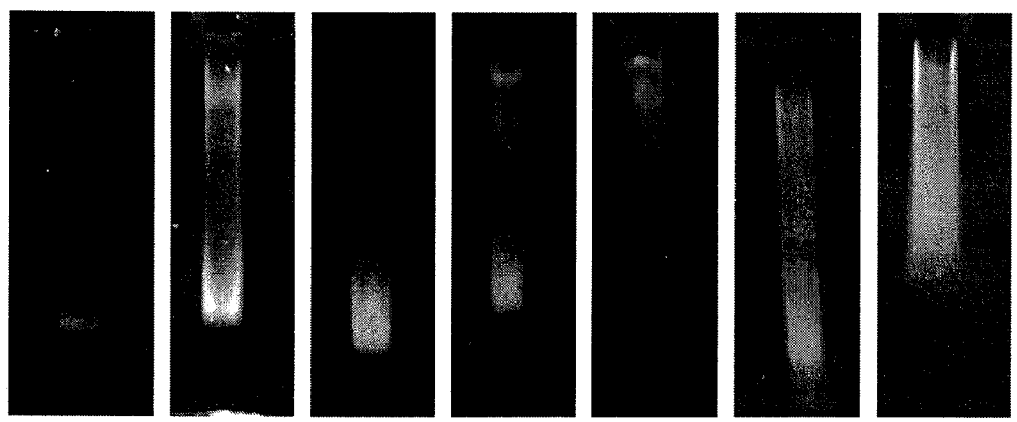
FIG. 20 shows the late rounds of SELEX. The first, second, third, fourth, fifth, sixth and seventh lanes are for the ninth, twelfth, thirteenth, fifteenth, sixteenth, seventeenth, and twenty-first round SELEX respectively. The gel shift assays were carried out as described in Methods. The ninth and twelfth round contained 1.5 μM enzyme, 1.5 μM ssDNA and 10 mM NaCl. The thirteenth and fifteenth round contained 1.5 μM Enzyme, 1.5 μM ssDNA and 15 mM NaCl. The sixteenth round contained 1.5 μM enzyme, 1.5 μM ssDNA and 20 mM NaCl. The seventeenth and twenty-first round contained 1.5 μM enzyme, 1.5 μM ssDNA and 50 mM NaCl.

A significant advantage of the electrophoretic separation is that it allows visualization of each selection step, making apparent the relative amounts of bound and free DNA. It thus indicates the stringency of selection and reveals whether ligand binding has occurred during the course of an experiment. In the early rounds (FIG. 16), the enzyme was in excess, so location of the enzyme:ssDNA complex was easily accomplished. The ratio of enzyme:ssDNA in early rounds was 6.7. The ratio was then gradually decreased to give more stringency of selection in the middle rounds (FIG. 18). The ratio of enzyme:ssDNA was 3.3, 3.3 and 1.3 at rounds 6, 7 and 8 respectively. The gel showed an enzyme:ssDNA complex (FIG. 18) that was more intense than the band corresponding to free DNA. From the ninth round, the ratio of enzyme:ssDNA was maintained at 1:1. The concentration of the NaCl added was increased to 15 mM from 10 mM at the thirteenth round. In the late rounds, free ssDNA was the predominately visible species in the gel (FIG. 20). In the sixteenth round, although the concentration of NaCl was increased up to 20 mM NaCl, free ssDNA was significantly diminished due to selection of high affinity of the ssDNA for the enzyme (FIG. 20).

Figure 17:
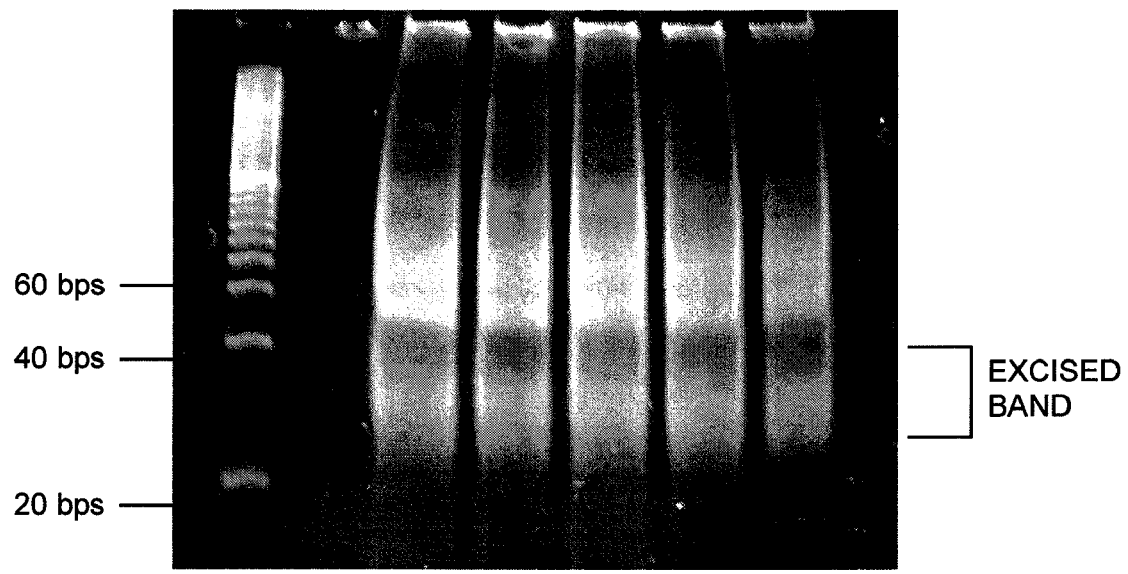
FIG. 17 shows a PCR of ssDNA from the first round of SELEX. The condition of the PCR was described in Methods. The first lane contained the molecular size markers. The first marker from the bottom represents 20 bps. The band excised was chosen because its migration on an 8 M urea gel matched the migration of the initial random ssDNA.
Figure 19:
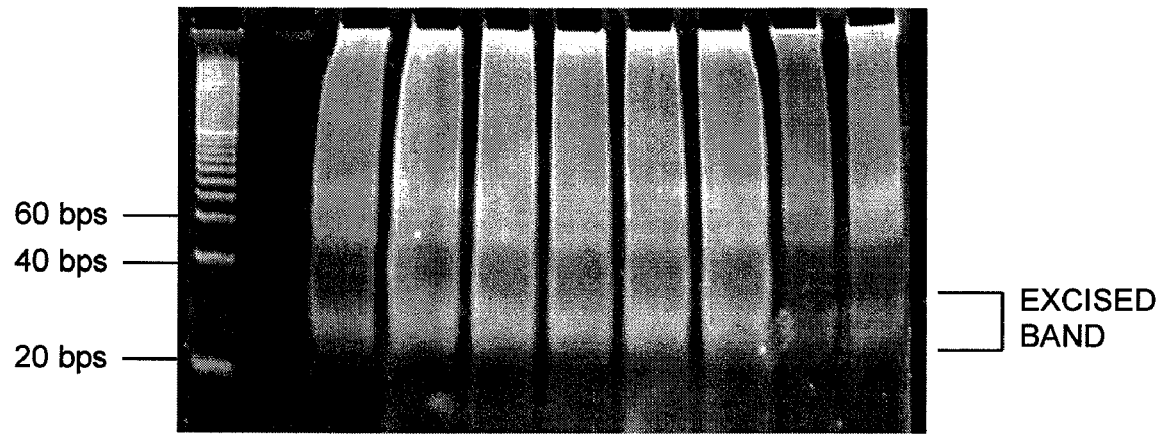
FIG. 19 shows a PCR of ssDNA from the ninth round of SELEX. The condition of the PCR was described in Methods. The first lane contained the molecular size markers. The first marker from the bottom represents 20 bps. The band excised was chosen because its migration on the 8 M urea gel matched the migration of the initial random ssDNA.
Figure 21:
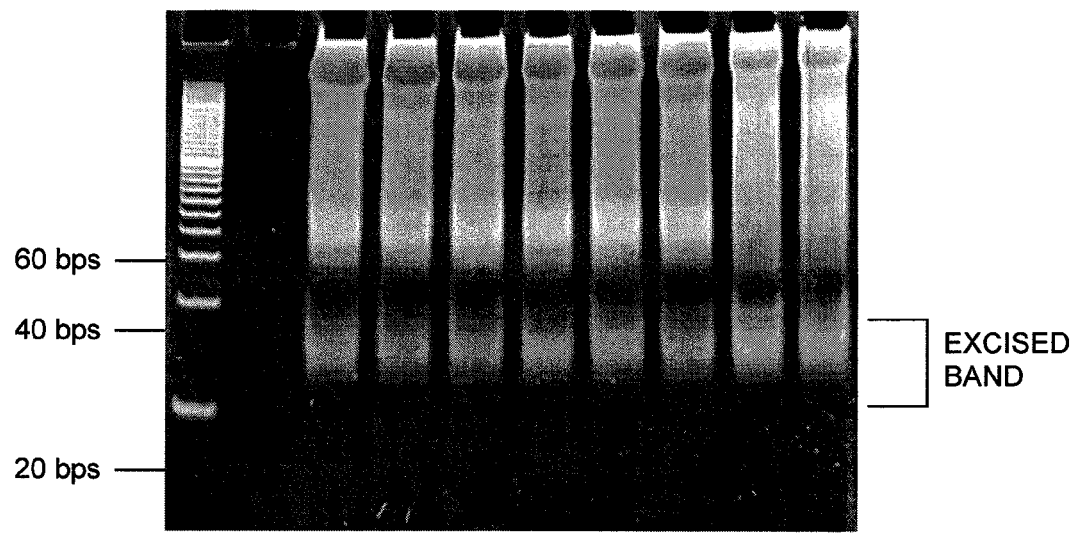
FIG. 21 shows a PCR of ssDNA from the twenty-first round of SELEX. The condition of the PCR was described in Methods. The first lane contained the molecular size markers. The first marker from the bottom represents 20 bps. The band excised was chosen because its migration on the 8 M urea gel matched the migration of the initial random ssDNA.

The PCR products of ssDNA were located between 20 bps and 40 bps (FIGS. 17, 19 and 21). To test whether the ssDNA could bind and inhibit the enzyme, a preliminary inhibition test was performed at the eighth, eleventh, fourteenth and sixteenth rounds. The results of preliminary inhibition study are summarized in Table 3.

At round 8, 40% inactivation occurred. After round 11, the inactivation increased to 75%. The inactivation of round 11 was very close to round 14. The inactivation of round 16, however, decreased to 53%. In this preliminary inhibition test, the results were not accurate because the concentration of ssDNA was estimated optically based on the intensity of florescence compared to the sample of ssDNA of known concentration.

After the sixteenth round, cloning of the fragment into the vector pRE2 was carried out. This made it possible to sequence the insert. The sequence was SeqID# 3-5'-d(ANC-NANNNTTNNNTNGNNGNNCATNNNNAA)-3', which contained 17 N's. To give more stringency of selection, beginning with the seventeenth round, the concentration of NaCl was increased to 50 mM. Also, the incubation time was increased to 2.5 hours. This resulted in a smearing effect on the gel due to increasing the salt concentration to 50 mM NaCl. After the twenty-first round, the cloning and sequencing were carried out again. The sequence of the 30-mer aptamer was determined to be SeqID# 4:

5'-d(AACCAAACTTGGATCGGTGCACATGTCGAA)-3'

This final single-stranded DNA aptamer (30-mer) was synthesized using a Beckman Oligo 1000M oligonucleotide synthesizer.

The $IC_{50}$ value for the 30-mer was determined by measuring the rate of enzymatic hydrolysis of cephalosporin C after the enzyme has been preincubated and assayed in presence of different of amounts of the 30-mer. The $IC_{50}$ of the 30-mer was 1.2 nM. The data is presented in Table 4 and FIG. 22. From a steady-state kinetic study, the 30-mer showed a non-competitive inhibition (FIG. 23). The value of $K_i$ (dissociation constant for the inhibitor from the enzyme-inhibitor complex) for the 30-mer was 0.92 nM and the value of $K_i'$ (dissociation constant for the inhibitor from the enzyme-substrate-inhibitor complex) for the 30-mer was 11 nM as determined by slope and intercept replots (Table 4, FIGS. 24 and 25).

In order to check to see if the reversible inhibition was time-dependent, the time dependence of the inhibition of the enzyme by 0.5 nM the 30-mer was measured. As can be seen from FIG. 26, the inhibition was time-independent.

Figure 27:
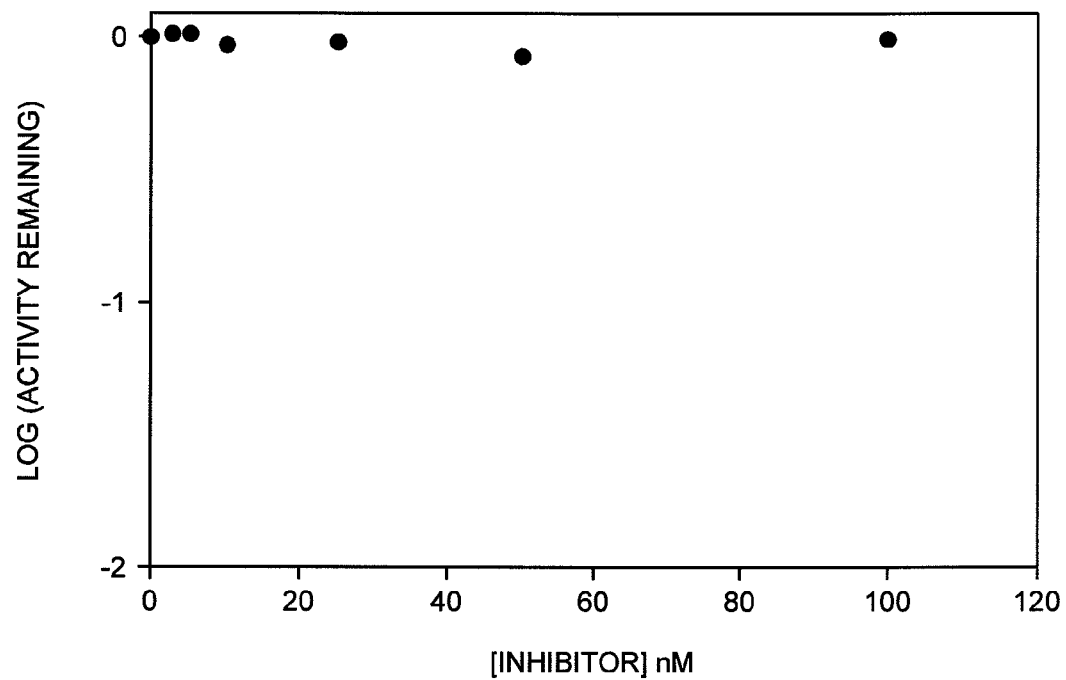

The experiment of FIG. 27 was performed to test the specificity of inhibition by this 30-mer. As can be seen, 100 nM of the 30-mer has no effect on the activity of the *B. cereus* 569/H/9 β-lactamase I (a class A β-lactamase).

Figure 28:
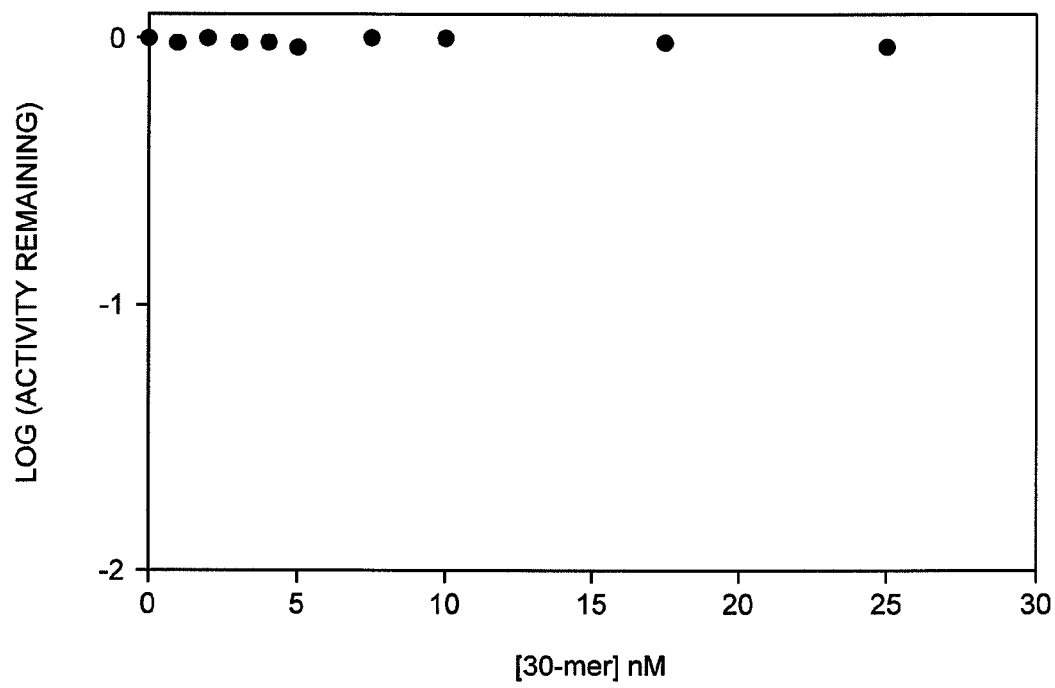

In addition, the bovine carboxypeptidase A was used to test the specificity of inhibition by this 30-mer. As can be seen in FIG. 28, 25 nM of the 30-mer has no effect on the activity of the carboxypeptidase A.

FIG. 13. The evidence for a complex of the *B. cereus* 5/B/6 metallo-β-lactamase and the ssDNA. On the left, the gel was stained by ethidium bromide. On the right, the gel was stained by Coomassie Brilliant Blue R250. 20 μM enzyme and 1.5 μM ssDNA were used to make the complex. The buffer used for incubation was 20 mM TA (pH=7.0) and 1 mM $ZnSO_4$.

FIG. 14. Comparison of the initial random ssDNA with the ssDNA after SELEX on a native gel. The first lane contained initial random ssDNA. The second lane contained the molecular size markers. The first marker from the bottom represents 20 bps. The fourth, fifth, sixth and seventh lanes contained PCR products after the eight round of SELEX. A 12% (w/v) polyacrylamide gel (29:1 mono:bis) was used in TA buffer.

FIG. 15. Comparison of the initial random ssDNA with the ssDNA after SELEX on a denaturing gel. The left lane contained ssDNA after SELEX and the right lane contained initial random ssDNA. The 12% polyacrylamide gel (29:1 mono:bis) was run with 8M urea in TBE buffer (45 mM Tris, 45 mM boric acid and 1 mM EDTA, pH=8.0).

Figure 16:
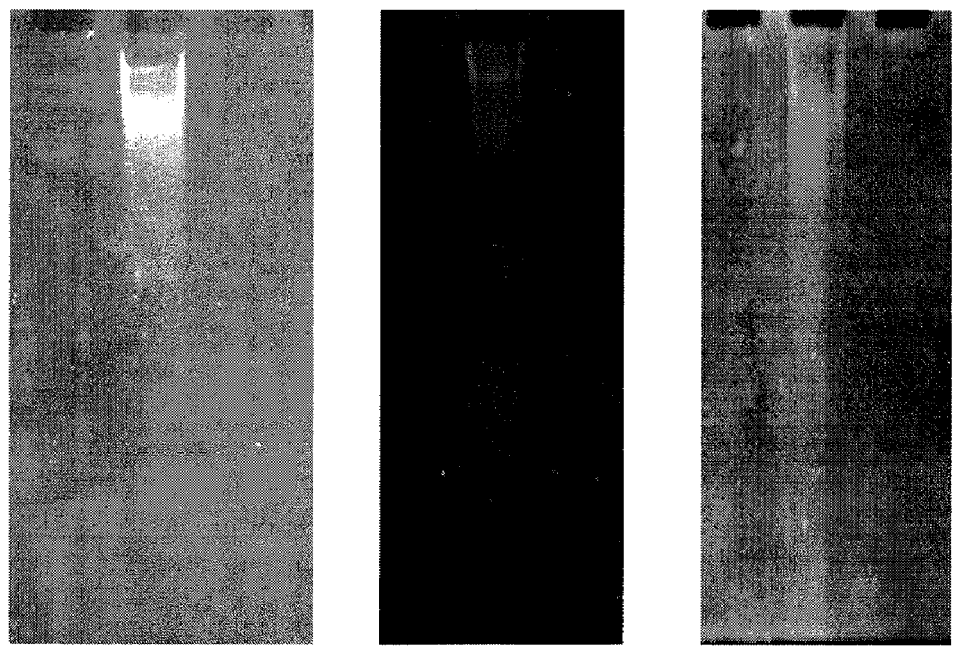
FIG. 16 shows the early rounds of SELEX. The first, second, third lanes are for the first, third, fifth rounds of SELEX respectively. The gel shift assays were carried out as described in Methods. The first round contained 20 μM enzyme, 3 μM ssDNA and 10 mM NaCl. The third round contained 20 μM enzyme, 1.5 μM ssDNA and 10 mM NaCl. The fifth round contained 10 μM enzyme, 1.5 μM ssDNA and 10 mM NaCl.

FIG. 16. The early rounds of SELEX. The first, second, third lanes are for the first, third, fifth rounds of SELEX, respectively. The gel shift assays were carried out as described in Methods. The first round contained 20 μM enzyme, 3 μM ssDNA and 10 mM NaCl. The third round contained 20 µM enzyme, 1.5 µM ssDNA and 101 NaCl. The fifth round contained 10 µM enzyme, 1.5 µM ssDNA and 10 mM NaCl.

FIG. 17. PCR of ssDNA from the first round of SELEX. The condition of the PCR was described in Methods. The first lane contained the molecular size markers. The first marker from the bottom represents 20 bps. The band excised was chosen because its migration on the 8 M urea gel matched the migration of the initial random ssDNA.

FIG. 18. The middle rounds of SELEX. The first, second, third lanes are for the sixth, seventh, eighth round SELEX, respectively. The gel shift assays were carried out as described in Methods. The sixth round contained 5 µM enzyme, 1.5 µM ssDNA and 10 mM NaCl. The seventh round contained 5 µM enzyme, 1.5 µM ssDNA and 10 mM NaCl. The eighth round contained 2 µM enzyme, 1.5 µM ssDNA and 10 mM NaCl.

FIG. 19. PCR of ssDNA from the ninth round of SELEX. The condition of the PCR was described in Methods. The first lane contained the molecular size markers. The first marker from the bottom represents 20 bps. The band excised was chosen because its migration on the 8 M urea gel matched the migration of the initial random ssDNA.

FIG. 20. The late rounds of SELEX. The first, second, third, fourth, fifth, sixth and seventh lanes are for the ninth, twelfth, thirteenth, fifteenth, sixteenth, seventeenth, and twenty-first round SELEX respectively. The gel shift assays were carried out as described in Methods. The ninth and twelfth round contained 1.5 µM enzyme, 1.5 µM ssDNA and 10 mM NaCl. The thirteenth and fifteenth round contained 1.5 µM Enzyme, 1.5 µM ssDNA and 15 mM NaCl. The sixteenth round contained 1.5 µM enzyme, 1.5 µM ssDNA and 20 mM NaCl. The seventeenth and twenty-first round contained 1.5 µM enzyme, 1.5 µM ssDNA and 50 mM NaCl.

FIG. 21. PCR of ssDNA from the twenty-first round of SELEX. The condition of the PCR was described in Methods. The first lane contained the molecular size markers. The first marker from the bottom represents 20 bps. The band excised was chosen because its migration on the 8 M urea gel matched the migration of the initial random ssDNA.

TABLE 3

Estimates of the metallo-β-lactamase activity assay in presence of selected ssDNA pools.

| Inhibitor DNA | Percent control enzyme activity |
|---|---|
| Oligonucleotides before SELEX | 100% |
| ssDNA* after the eighth round | 60% |
| ssDNA* after the eleventh round | 25% |
| ssDNA* after the fourteenth round | 27% |
| ssDNA* after the sixteenth round | 47% |

*The approximate concentration of the ssDNA was estimated as described in the text to be 42 nM.

Figure 22:
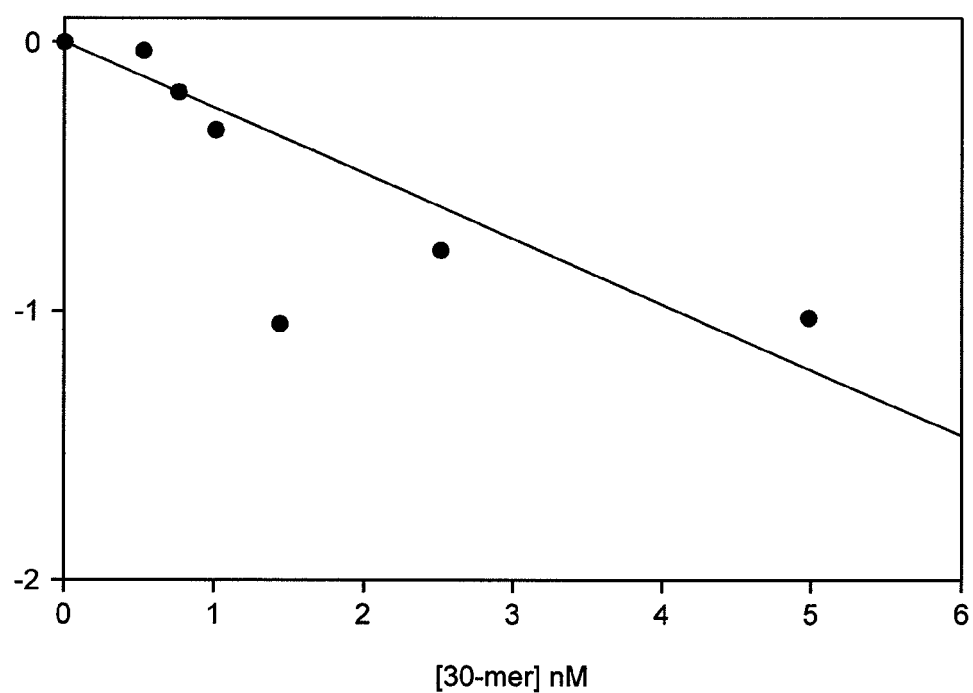
FIG. 22 shows a determination of $IC_{50}$ for B. cereus 5/B/6 metallo-β-lactamase by the 30-mer. The enzyme was incubated in the buffer (50 mM MOPS, pH=7.0) for the 15 min. at 30° C. The concentration of the substrate (cephalosporin C) was 4 mM.
Figure 23:
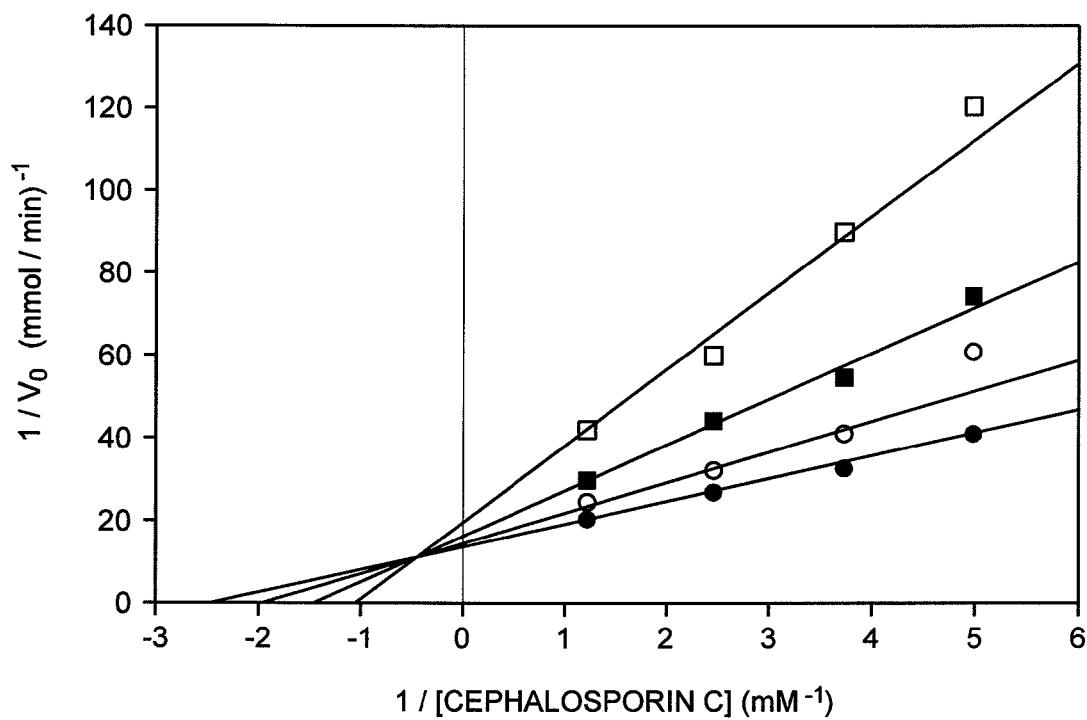
FIG. 23 shows a Lineweaver-Burk plot of inhibition of B. cereus 5/B/6 metallo-β-lactamase by the 30-mer. Filled circle: [I]=0 nM, open circle: [I]=1 nM, filled square: [I]=2 nM; open square: [I]=3 nM. I=the 30-mer.

FIG. 22. Determination of $IC_{50}$ for B. cereus 5/B/6 metallo-β-lactamase by the 30-mer. The enzyme was incubated in the buffer (50 mM MOPS, pH=7.0) for the 15 min. at 30° C. The concentration of the substrate (cephalosporin C) was 4 mM.

FIG. 23. Lineweaver-Burk plot of inhibition of B. cereus 5/B/6 metallo-β-lactamase by the 30-mer. Filled circle: [I]=0 nM; open circle: [I]=1 nM; filled square: [I]=2 nM; open square: [I]=3 nM. I=the 30-mer.

Figure 24:
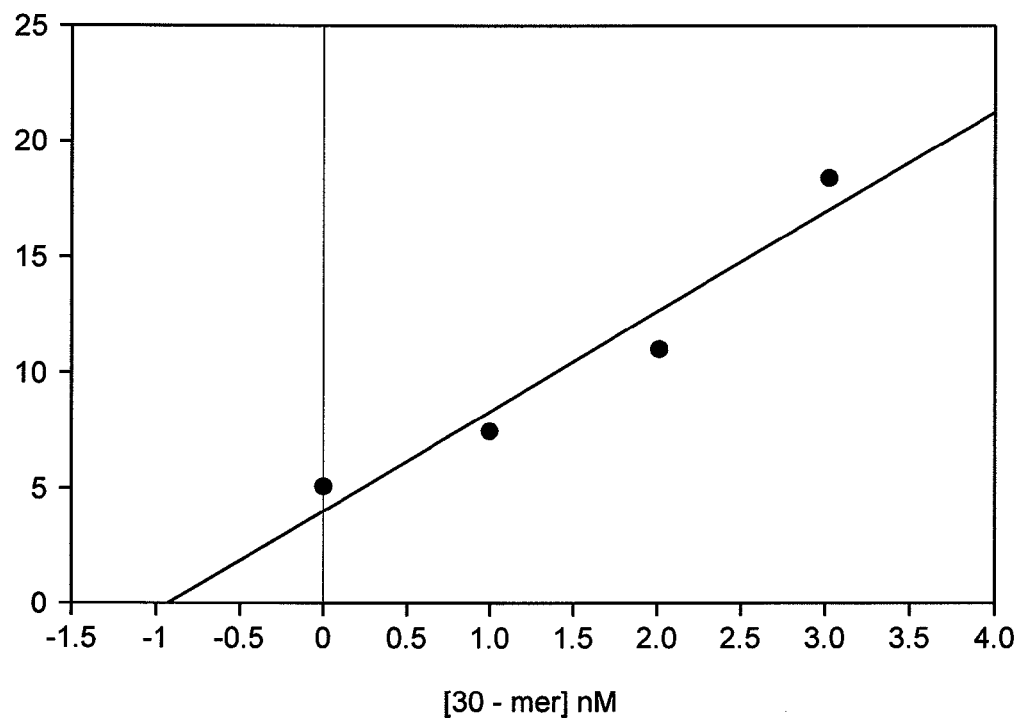
FIG. 24 shows a slope replot to estimate $K_i$ for the 30-mer. Slope values ($K_m/V_{max}$) for each inhibitor concentration from experimental data of FIG. 23 were determined using a non-linear regression computer program (EnzymeKinetics, v. 1.2, Trinity Software). Slope values were then plotted vs. corresponding inhibitor concentrations. The x-intercept in this plot is $-K_i$.

FIG. 24. Slope replot to estimate $K_i$ for the 30-mer. Slope values ($K_m/V_{max}$) for each inhibitor concentration from experimental data of FIG. 23 were determined using a non-linear regression computer program EnzymeKinetics, v. 1.2, Trinity Software). Slope values were then plotted vs. corresponding inhibitor concentrations. The x-intercept in this plot is $-K_i'$.

Figure 25:
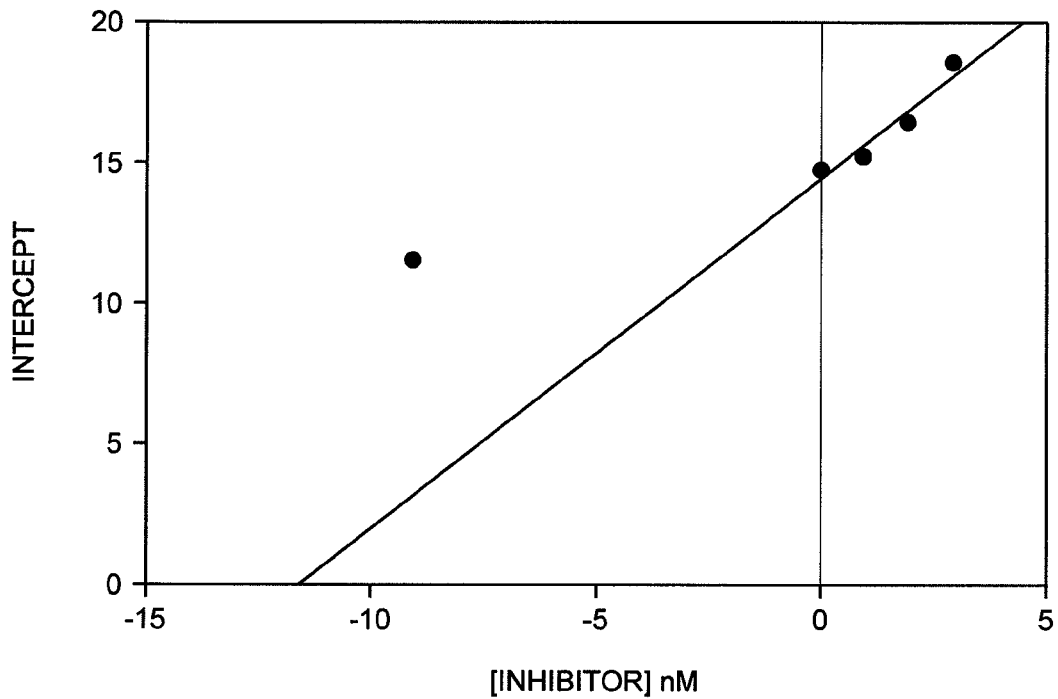
FIG. 25 shows a intercept replot to estimate $K_i'$ for the 30-mer. Intercept values ($1/V_{max}$) for each inhibitor concentration from experimental data of FIG. 23 were determined using a non-linear regression computer program (EnzymeKinetics, v. 1.2, Trinity Software). Intercept values were then plotted vs. corresponding inhibitor concentrations. The x-intercept in this plot is $-K_i'$.

FIG. 25. Intercept replot to estimate $K_i'$ for the 30-mer. Intercept values ($1/V_{max}$) for each inhibitor concentration from experimental data of FIG. 23 were determined using a non-linear regression computer program (EnzymeKinetics, v. 1.2, Trinity Software). Intercept values were then plotted vs. corresponding inhibitor concentrations. The x-intercept in this plot is $-K_i'$.

Figure 26:
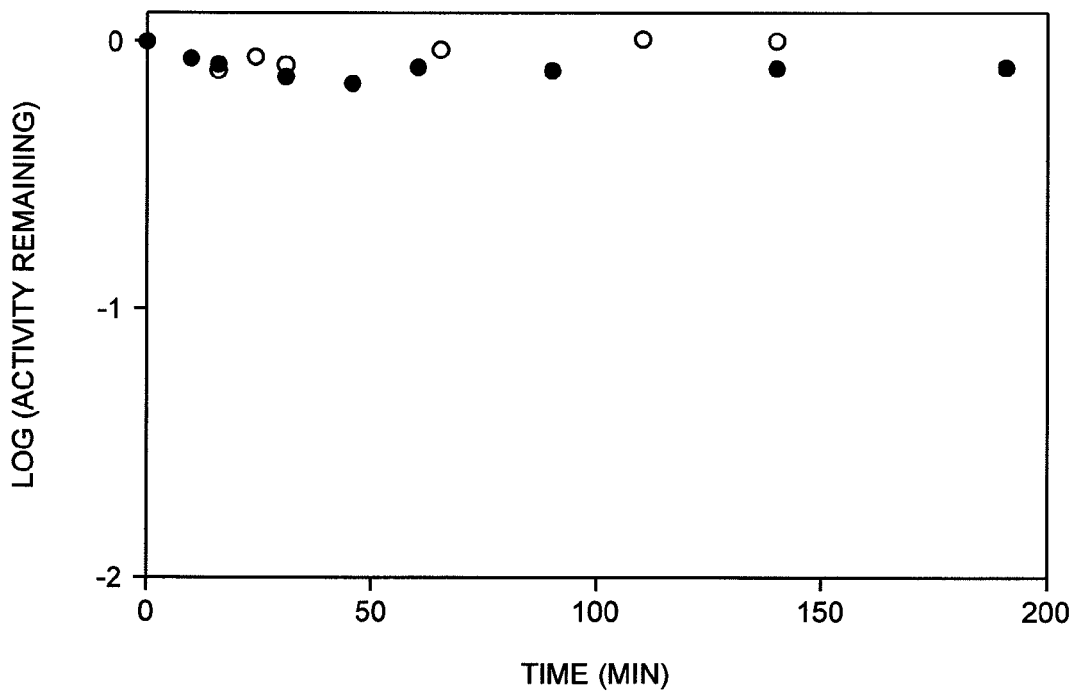

FIG. 26. Time-dependence of inactivation of B. cereus 5/B/6 metallo-β-lactamase activity by the 30-mer. The concentration of the 30-mer was 0.5 nM. Incubation and assay buffer was 50 mM MOPS, pH=7.0. cephalosporin C was used as substrate. Open circle: [I]=0 filled circle: [I]=0.5 mM. I=the 30-mer.

FIG. 27. Effect of various concentrations of the 30-mer on B. cereus 569/H/9 β-lactamase I. The enzyme was preincubated with/without the inhibitor in the buffer (50 mM MOPS, pH=7.0) for the 15 min. at 30° C. The concentration of the substrate (benzylpenicillin) was 1.1 mM.

FIG. 28. Inhibition of bovine carboxypeptidase A by various concentrations of the 30-mer. The enzyme was preincubated with/without the inhibitor in the buffer (0.05 M TrisHCl, pH=7.5 with 0.5 M sodium chloride) for the 15 min. at 25° C. The concentration of the substrate (hippuryl-L-phenylalanine) was 1 nM

TABLE 4

Inhibition of B. cereus 5/B/6 metallo-β-lactamase by the ssDNA 30-mer.

| | $IC_{50}$ | $K_i$ | $K_i'$ |
|---|---|---|---|
| Synthetic 30-mer | 1.2 nM | 0.92 nM | 11 nM |

Prediction of Secondary Structure of Aptamers and Metallo-β-lactamase Inhibition The secondary structure of aptamers was predicted by the MFold program (Zuker, 1989). Two different secondary structures of the aptamer (30-mer) were predicted.

Figures 29, 30, 31:
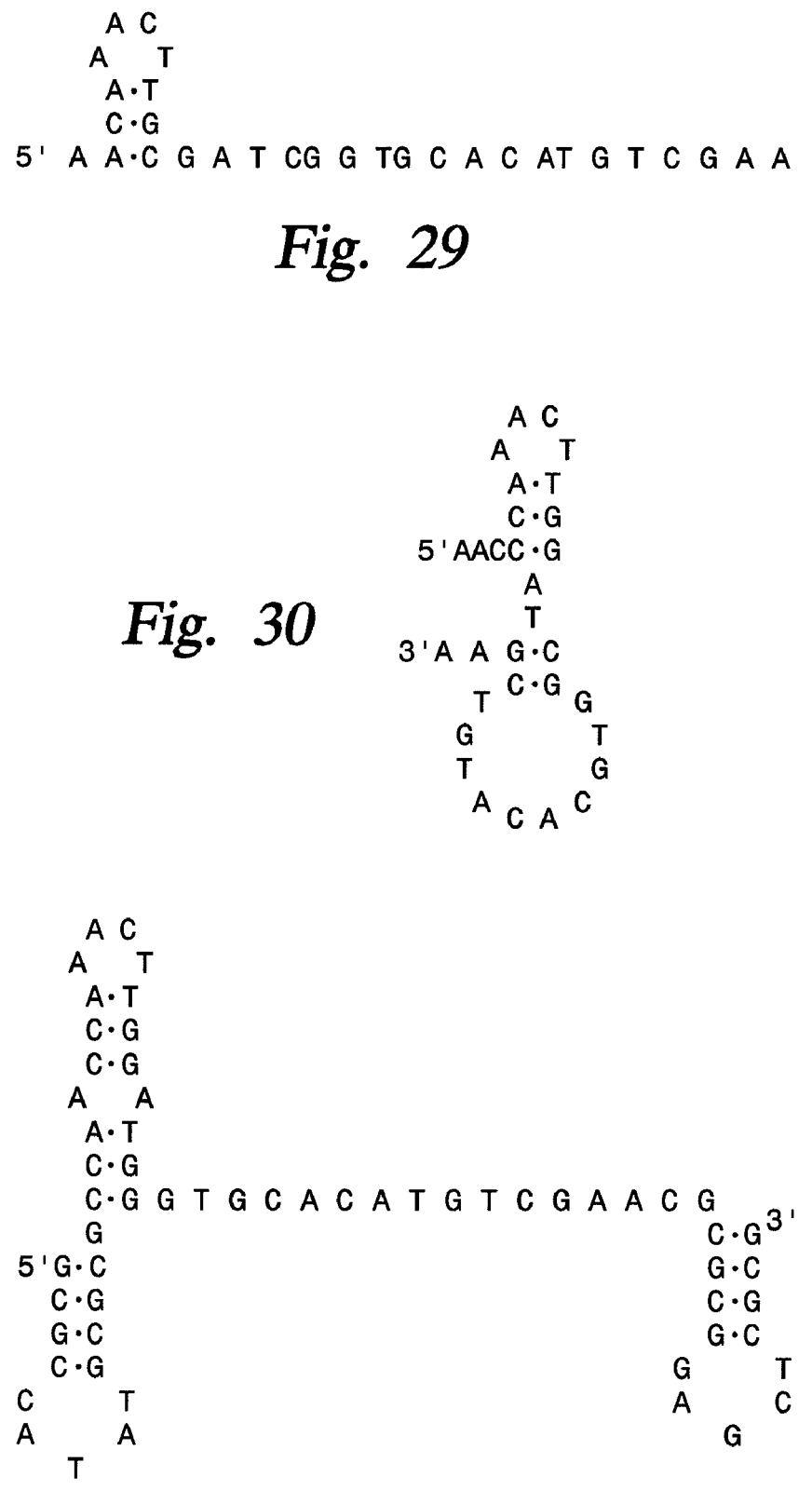

SeqID# 4 is a 30 mer ssDNA and is shown in Structure 1 (FIG. 29) included a one stem-loop structure, and structure 2 FIG. 30) included a two stem-loop structure. Structure 1 was predicted to be lower in energy than structure 2. The sequence of the stem-loop structure from structure 1 is 5'-d(CCAAACTTGG)-3'. This sequence is one of the two stem-loop structures from structure 2 as well. The thermodynamic parameters of folding of the aptamers were calculated by MFold program (Table 5).

The predicted secondary structure for the aptamer (61-mer) as listed in SeqID# 6 containing the primer sequence regions revealed several stem-loop structures (FIG. 31). The sequence SeqID# 5, 5'-d(CCAAACTTGG)-3', was present as a stem-loop structure in the aptamer (61-mer). This result suggests that the SeqID# 5 5'-d(CCAAACTTGG)-3' sequence may be important for interaction with metallo-β-lactamase.

This conserved single-stranded DNA (10-mer) SeqID# 5 sequence was synthesized using a Beckman Oligo 1000M oligonucleotide synthesizer. To confirm the stem-loop structure from the conserved sequence, the secondary structure of the 10-mer was predicted by the Wold program (Zuker, 1989). From the prediction, the same stem-loop secondary structure of the 10-mer was preserved FIG. 32).

The IC$_{50}$ value for the SeqID# 5 10-mer was determined by measuring the rate of enzymatic hydrolysis of cephalosporin C after the enzyme has been preincubated and assayed in presence of different amounts of the 10-mer. The data is presented in Table 6 and FIG. 33.

Figure 34:
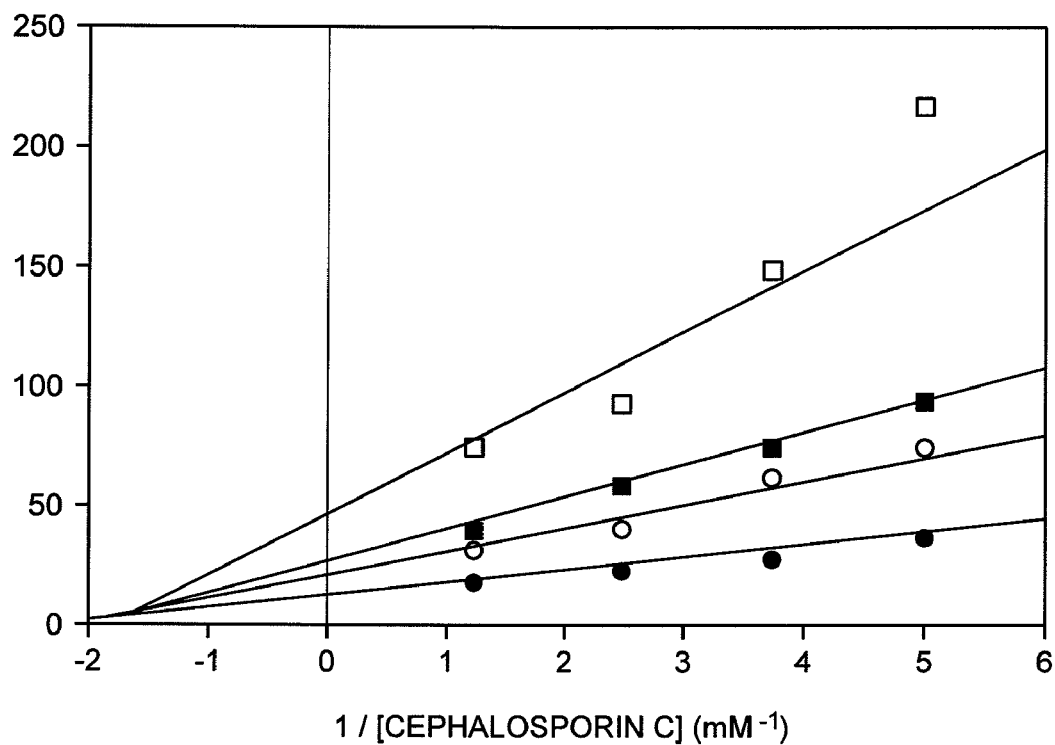

From a steady-state kinetic study, the 10-mer SeqID# 5 showed a noncompetitive inhibition (FIG. 34). The value of K$_i$ (dissociation constant for the inhibitor from the enzyme-inhibitor complex) for the 10-mer was 0.31 nM and the value of K$_i$' (dissociation constant for the inhibitor from the enzyme-substrate-inhibitor complex) for the 10-mer was 1.5 nM as determined by slope and intercept replots (Table 6, FIGS. 35 and 36).

In order to check to see if the reversible inhibition was time-dependent, the time dependence of the inhibition of the enzyme by 1.0 nM of the 10-mer was measured. As can be seen from FIG. 37, the inhibition was time-independent.

Figure 38:
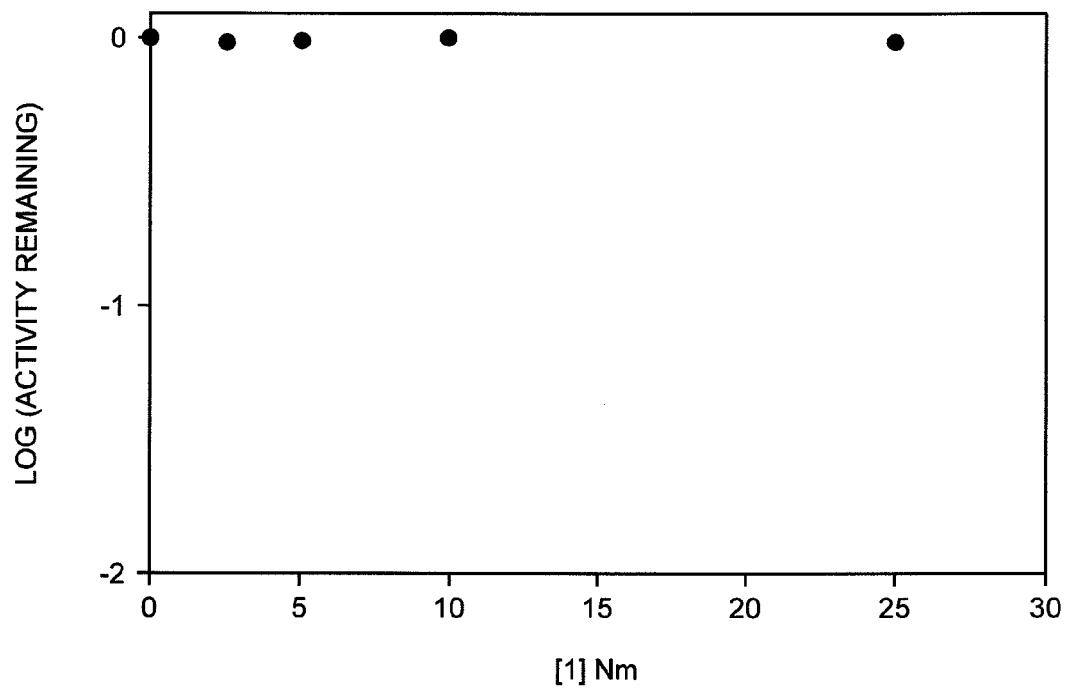

The experiment of FIG. 38 was performed to test the specificity of inhibition by this 10-mer SeqID# 5. As can be seen, the 10-mer has no effect on the activity of the *B. cereus* 569/H/9 β-lactamase I (a class A β-lactamase).

Figure 39:
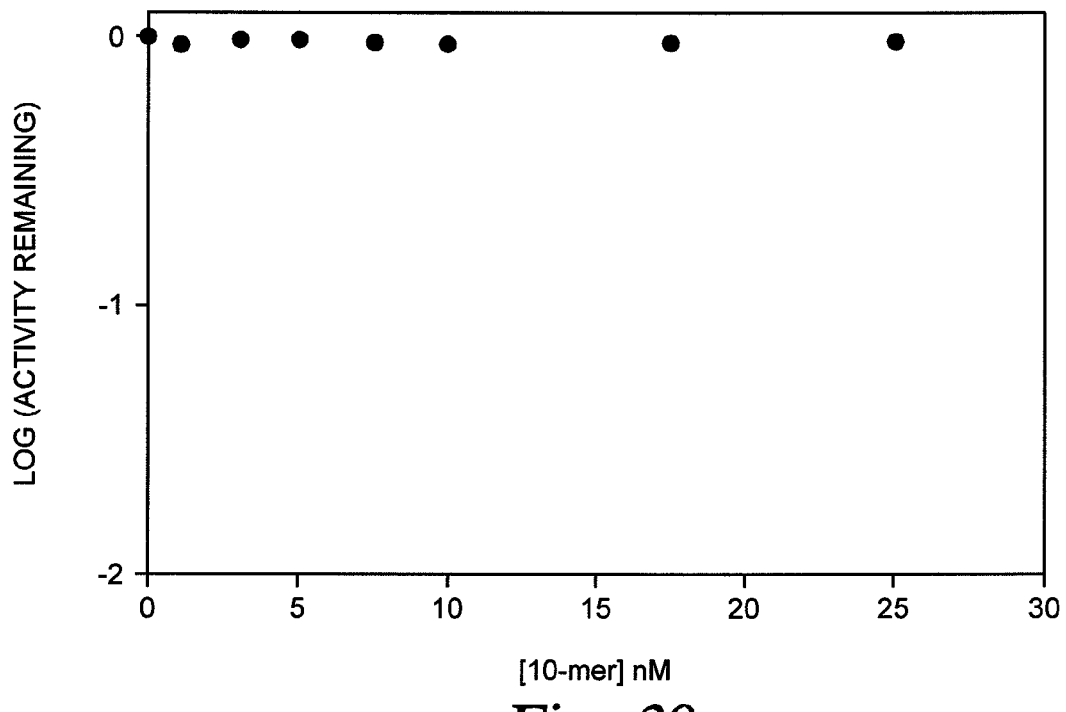

In addition, the bovine carboxypeptidase A was used to test the specificity of inhibition by this 10-mer. As can be seen in FIG. 39, 25 nM of the 10-mer has no effect on the activity of the carboxypeptidase A.

Figure 40:
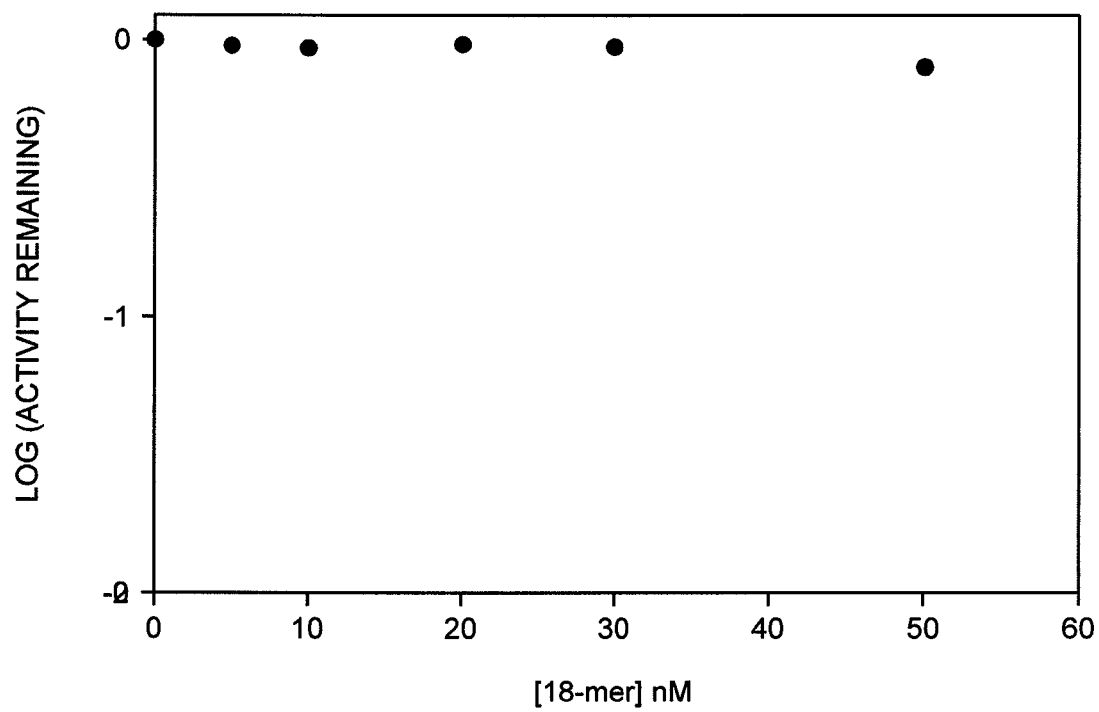

An 18-mer corresponding to the remainder of the 30-mer sequence was tested to check how much the conserved 10-mer from the prediction is responsible for the inhibition of the metallo-β-lactamase. As can be seen in FIG. 40, the 18-mer did not show significant inhibition up to 50 nM.

Figure 41:
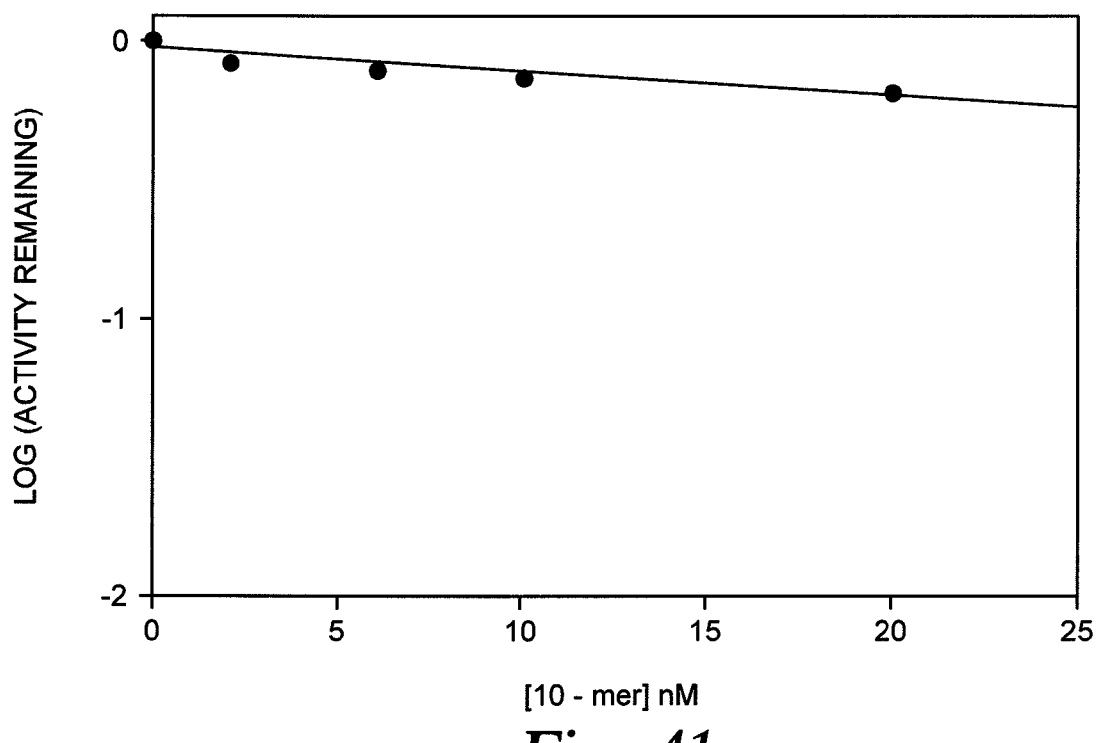

As a control experiment, in order to check to see if the 10-mer binds to metal ion(s) in the active site of the metallo-β-lactamase, the assay for the metallo-β-lactamase was carried out in the presence of 1 mM ZnSO$_4$. The IC$_{50}$ value for the 10-mer was greatly elevated up to 32 nM because of the excess Zn$^{2+}$ ions (FIG. 41).

FIG. 29. Secondary structure 1 of the 30-mer predicted by the MFold program (Zuker, 1989).

FIG. 30. Secondary structure 2 of the 30-mer predicted by the MFold program (Zuker, 1989).

FIG. 31. Secondary structure of the 61-mer (SeqID# 6) predicted by the MFold program (Zuker, 1989).

TABLE 5

Calculation of thermodynamic parameters for folding of ssDNA aptamers in 50 mM NaCl at 30° C.* by MFold program

| | $-\Delta G$ (kcal/mole) | $-\Delta H$ (kcal/mole) | $-\Delta S$ (cal/K mol)) | T$_m$ (° C.) |
|---|---|---|---|---|
| Structure 1 of the 30-mer | 2.2 | 29.9 | 91.4 | 54.1 |
| Structure 2 of the 30-mer | 2.2 | 50.3 | 158.7 | 43.9 |
| Structure of the 61-mer | 11.4 | 123.4 | 369.5 | 60.9 |
| Structure of the 10-mer | 0.5 | 21.5 | 69.3 | 37.2 |

*Temperature and the concentration of NaCl are the same conditions as the SELEX experiments.

Figure 32:
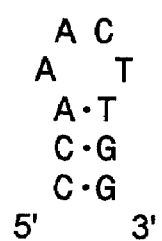

FIG. 32. Secondary structure of the 10-mer produced by the MFold program (Zuker, 1989).

Figure 33:
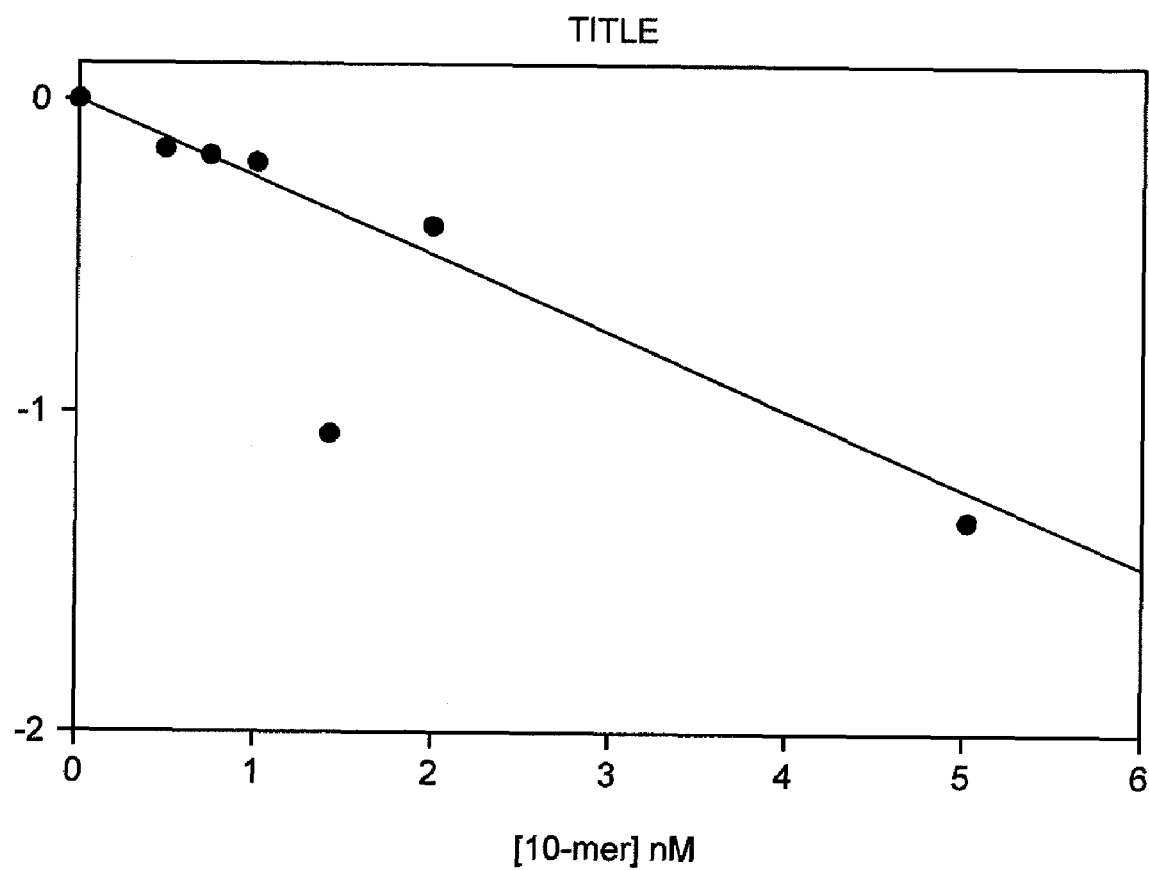

FIG. 33. Determination of IC$_{50}$ for *B. cereus* 5/B/6 metallo-β-lactamase by the 10-mer. The enzyme was preincubated with/without the inhibitor in the buffer (50 mM MOPS, pH=7.0) for the 15 min. at 30° C. The concentration of the substrate (cephalosporin C) was 4 mM.

FIG. 34. Lineweaver-Burk plot of inhibition of *B. cereus* 5/B/6 metallo-β-lactamase by the 10-mer. Filled circle: [I]=0 nM; open circle: [I]=1 nM; filled square: [I]=2 nM open square: [I]=3 nM. I=the 10-mer.

Figure 35:
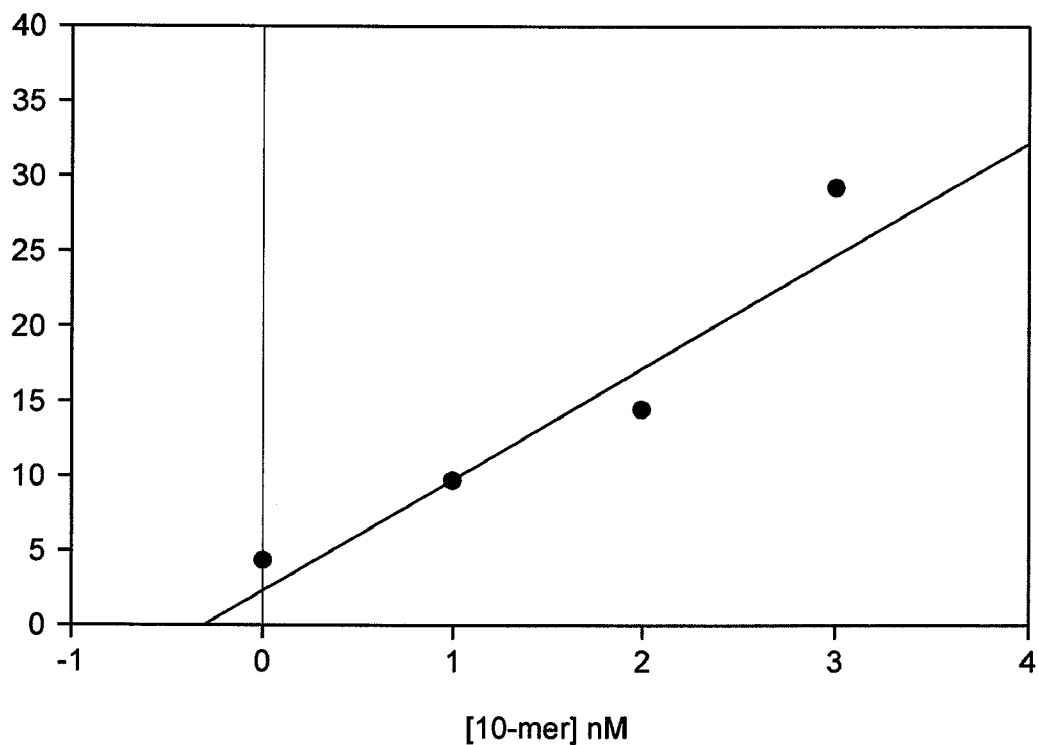

FIG. 35. Slope replot to estimate K$_i$ for the 10-mer. Slope values (K$_m$/V$_{max}$) for each inhibitor concentration from experimental data of FIG. 34 were determined using a non-linear regression computer program (EnzymeKinetics, v. 1.2, Trinity Software). Slope values were then plotted vs. corresponding inhibitor concentrations. The x-intercept in this plot is $-K_i$.

Figure 36:
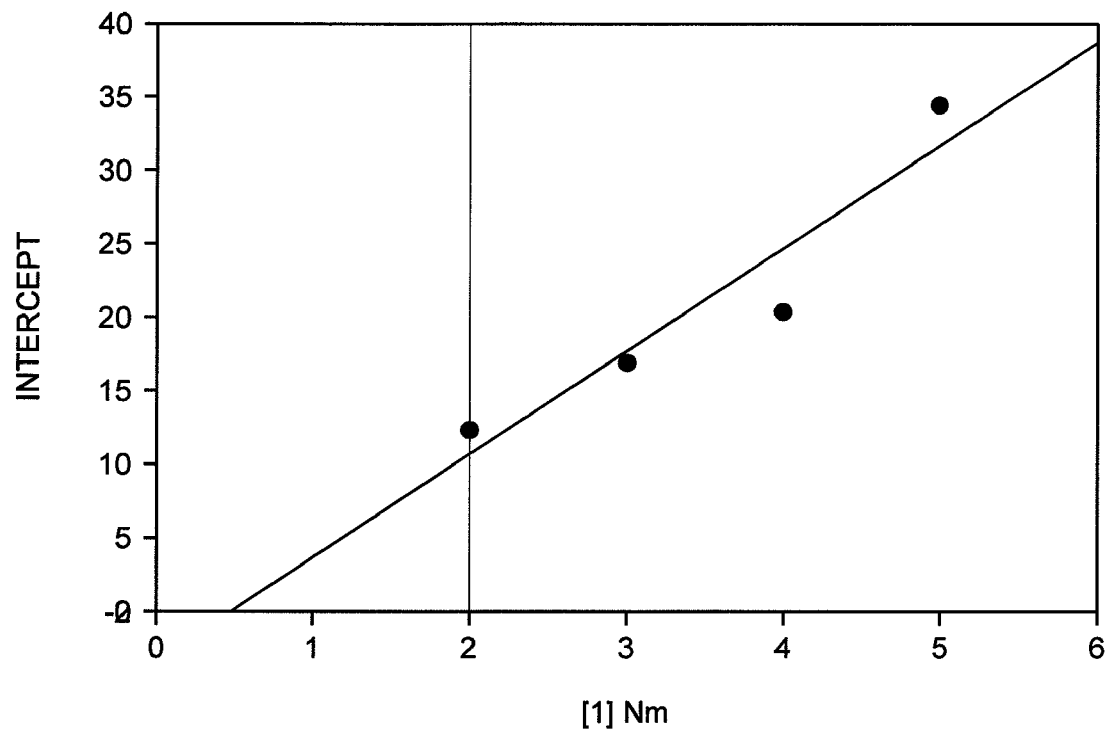

FIG. 36. Intercept replot to estimate K$_i$' for the 10-mer. Intercept values (1/V$_{max}$) for each inhibitor concentration from experimental data of FIG. 34 were determined using a non-linear regression computer program (EnzymeKinetics, v. 1.2, Trinity Software). Intercept values were then plotted vs. corresponding inhibitor concentrations. The x-intercept in this plot is $-K_i'$.

Figure 37:
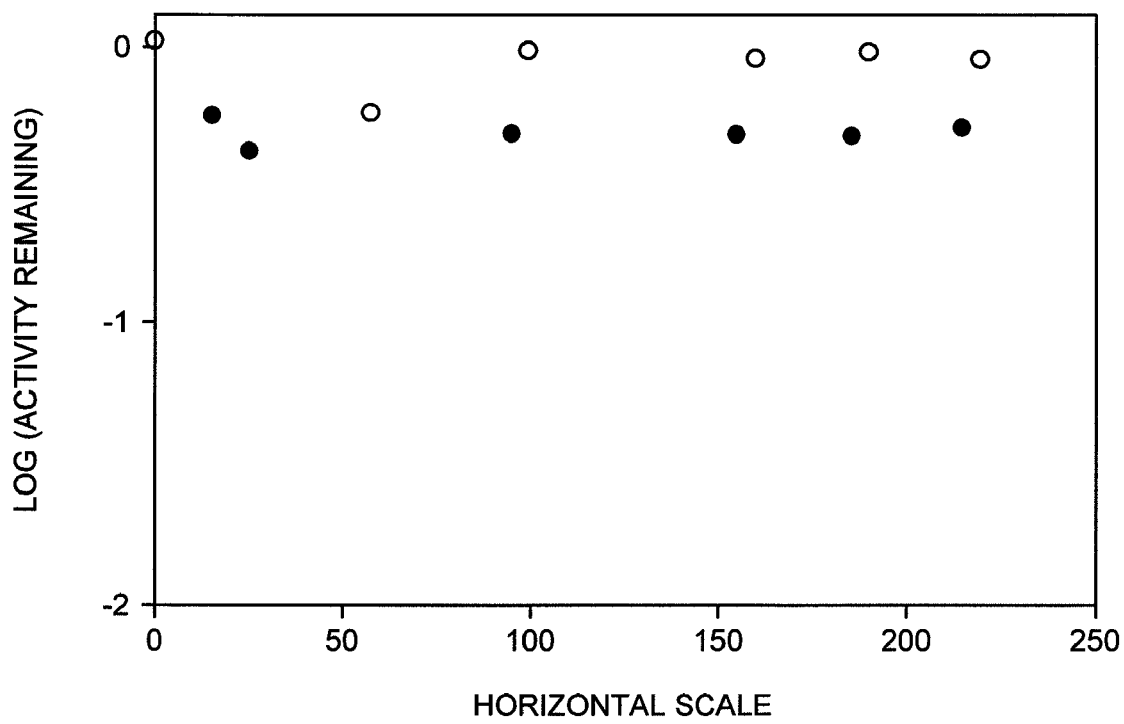

FIG. 37. Time-dependence of inactivation of *B. cereus* 5/B/6 metallo-β-lactamase activity by the 10-mer. The concentration of the 30-mer was 0.5 nM. Incubation and assay buffer was 50 mM MOPS, pH=7.0. cephalosporin C was used as substrate. Open circle: [I]=0 nM; filled circle: [I]=0.5 nM. I=the 10-mer.

FIG. 38. Inhibition of *B. cereus* 569/H/9 β-lactamase I by various concentrations of the 10-mer. The enzyme was preincubated with/without the inhibitor in the buffer (50 mM MOPS, pH=7.0) for the 15 min. at 30° C. The concentration of the substrate (benzylpenicillin) was 1.1 nM.

FIG. 39. Effect of various concentrations of the 10-mer on bovine carboxypeptidase A. The enzyme was preincubated with/without the inhibitor in the buffer (0.05 M TrisHCl, pH=7.5 with 0.5 M sodium chloride) for the 15 min. at 25° C. The concentration of the substrate (hippuryl-L-phenylalanine) was 1 mM.

FIG. 40. Inhibition of for *B. cereus* 5/B/6 metallo-β-lactamase by various concentrations of the 18-mer. The enzyme was preincubated with/without the inhibitor in the buffer (50 mM MOPS, pH=7.0) for the 15 min. at 30° C. The concentration of the substrate (cephalosporin C: was 4 mM.

FIG. 41. Determination of IC$_{50}$ for *B. cereus* 5/B/6 metallo-β-lactamase in the presence of Zn$^{2+}$ ions by the 10-mer. The enzyme was preincubated with/without the inhibitor in the buffer (50 mM MOPS and 1 mM ZnSO$_4$, pH=7.0) for the 15 min. at 30° C. The concentration of the substrate (cephalosporin C) was 4 nM

TABLE 6

Inhibition of *B. cereus* 5/B/6 metallo-β-lactamase by the ssDNA 10-mer.

| | IC$_{50}$ | K$_i$ | K$_i$' |
|---|---|---|---|
| Synthetic 10-mer | 1.2 nM | 0.31 nM | 1.5 nM |

As a preliminary experiment, inhibition patterns for EDTA and 2-mercaptoethanol were generated. From inhibition kinetic studies, noncompetitive inhibition was shown for EDTA and 2-mercaptoethanol. EDTA is well known as a good chelating reagent for Zn$^{2+}$ ions.

Metallo-β-lactamase inhibition studies by a combinatorial approach (SELEX). To find an inhibitor for metallo-β-lactamase, a combinatorial approach was utilized. In this study, we have taken advantage of the SELEX methodology to generate high affinity single-stranded DNA aptamers that inhibit metallo-β-lactamase activity.

To increase the stringency of selection during the course of the SELEX experiments, the concentrations of enzyme and NaCl were varied (Table 1). When the enzyme concentration was greater than the ssDNA concentration, the inhibition was approximately 40%; higher inhibition was detected after the enzyme concentration was decreased. This infers that the stringency of selection helped to eliminate non-specific binding of ssDNA. Increasing the concentration of NaCl also favored specific binding by ssDNA resulting in selection for a specific oligonucleotide sequence. As another factor in detecting aptamers, increasing the incubation time may be allowed to provide time for any conformational changes of the metallo-β-lactamase that might occur to "lock" onto the specific ssDNA strongly. In the early rounds, the bands of ssDNA PCR products on the gel were broad. The bands were getting sharper and more distinct throughout the SELEX rounds.

Following 21 rounds of SELEX, a single nucleic acid sequence was found. The 30-mer had $IC_{50}$ of 1.2 nM. From the kinetic study, noncompetitive inhibition was indicated for the 30-mer. The $K_i$ (dissociation constant for inhibitor from enzyme-inhibitor complex) and $K_i'$ (dissociation constant for inhibitor from enzyme-substrate-inhibitor complex) values were 0.92 nM and 11 nM, respectively. The noncompetitive inhibition pattern was similar to the noncompetitive inhibition patterns of EDTA and 2-mercaptoethanol. Therefore, the 30-mer is likely to bind to one or more $Zn^{2+}$ ions in the active site of the enzyme. The other possibility is that the 30-mer may interact with the enzyme in such a way as to block substrate access to the metal ions. This possibility could be tested by X-ray crystallographic analysis of the inhibited enzyme to determine the specific binding region of ssDNA.

This inhibition was not time-dependent. The 30-mer did not show any inhibition of β-lactamase I or carboxypeptidase A. Hence, the inhibition is very specific for metallo-β-lactamases. Clearly, the oligonucleotide does not recognize features in the metallo-β-lactamase that bind to the substrate. The carboxypeptidase A results show the exquisite specificity for the metal ion of metallo-β-lactamase. Carboxypeptidase A has been compared to the metallo-β-lactamase as a model for the latter enzyme, both in terms of structural and mechanistic features (Alberts et al., 1998: Bouagu et al., 1998). Hence, the demonstration that a concentration of the 30-mer that is 25×$IC_{50}$ for the metallo-β-lactamase has no effect on either 569/H/9 β-lactamase I activity or on the activity of bovine carboxypeptidase A are profound observations regarding the specificity of inhibition.

A major point is that while this is considerable evidence that suggests that the mode of inhibition involves metal binding by the inhibitor, it is clear that the inhibitor does not indiscriminately chelate all zinc from all sources as does EDTA or other metal chelators.

Payne et al., (1997) have identified inhibitors for metallo-β-lactamase. One of a mercaptoacetic acid thiol esters series (SB216968) inhibited *Aeromonas hydrophila* CphA metallo-β-lactamase and was found to be an uncompetitive inhibitor ($K_i$=3.9 µM). Yang and Crowder (1999) have also identified inhibitors for metallo-β-lactamase from *Stenotrophomonas maltophilia*. They showed that N-(2'-mercaptoethyl)-2-phenylacetamide and N-benzylacetyl-D-alanylthioacetic acid were competitive inhibitors with $K_i$ values of 50±3 µM and 1.6±0.3 µM, respectively. Scrofani et al. (1999) suggested that the inhibitor 3-[2'-(S)-benzyl-3'-mercaptopropanoyl]-4-(S)-carboxy-5,5-dimethylthiazolidine, that exhibits many structural similarities to the β-lactam antibiotic ampicillin, "tightly" binds in a position similar to that thought to be occupied by β-lactam antibiotics for metallo-β-lactamase from *B. fragilis* using NMR characterization. A free sulfhydryl group of the inhibitor did not show a disulfide formation with one of the free cysteine side chains in the vicinity of the zinc-binding site. Mollard et al. (2001) showed that thiomandelic acid was a competitive inhibitor of metallo-β-lactamases with $K_i$ values (*Bacillus cereus* enzyme) of 0.09 µM for R-thiomandelic acid and 1.28 µM for the S-isomer. To date, R-thiomandelic acid appears to be the most effective published inhibitor for metallo-β-lactamase. However, the $K_i$ value (0.92 nM) of the 30-mer that we found was more effective than any of the others. Therefore, the 30-mer is a very promising inhibitor for metallo-β-lactamase.

Prediction of secondary structure of aptamers and metallo-β-lactamase inhibition. It is desirable that the aptamer should be as small as possible, on costs grounds, reasons of target accessibility and so on. The predicted secondary structures of the 30-mer produced by the MFold program revealed a conserved stem-loop structure. The sequence was 5'-d (CCAAACTTGG)-3'. Hence, we synthesized the 10-mer.

The $IC_{50}$ of the 10-mer was the same as the 30-mer. From the steady-state kinetic studies, the noncompetitive inhibition pattern was shown like the 30-mer. The $IC_{50}$ value for the 10-mer was greatly elevated when the assay was carried out in the presence of inhibitor with exogenous $Zn^{2+}$ ions. This supports idea that the 10-mer likely binds to the metal ion(s).

The $K_i$ (dissociation constant for inhibitor from enzyme-inhibitor complex) and $K_i'$ (dissociation constant for inhibitor from enzyme-substrate-inhibitor complex) values were 0.31 nM (290-fold lower than the $K_i$ reported for R-thiomandelic acid (Mollard et al. (2001)) and 1.5 nM, respectively. The $K_i$ and $K_i'$ values for the 10-mer were lower than the 30-mer. This infers that the 10-mer binds the free enzyme and enzyme-substrate complex more strongly than the 30-mer. Although not wanting to be bound by theory the SeqID# 5 10-mer comprises a more promising drug candidate than the 30-mer SeqID# 4. For example, like the 30-mer, this inhibition was not time-dependent and the 10 mer did not show any inhibition for β-lactamase I and carboxypeptidase A. Hence, the inhibition is very specific for metallo-β-lactamases as well.

The secondary structure of 10-mer, as proposed by the MFold program, correlated well with the experimental results. The conserved structure from the sequence 5'-d (CCAAACTTGG)-3' is responsible for the inhibition of *B. cereus* 5/B/6 metallo-β-lactamase.

An example of a commercial product using SELEX technology, Eyetech Pharmaceuticals, Inc. has a product in clinical trials that is an aptamer that inhibits vascular endothelial growth factor (VEGF). The aptamer was discovered using SELEX (Jellinek et al., 1994; Ruckman et al., 1998; Willis et al., 1998). Known as EYE001, the aptamer is an oligonucleotide that acts like a high affinity antibody to VEGF. This anti-VEFG aptamer blocks vessel growth and inhibits neovascularization in pre-clinical models.

Single-stranded DNA (Bock et al., 1992; Macaya et al., 1995; Tsiang et al., 1995) was found using the SELEX process for thrombin that is a multifunctional serine protease. The DNA ligands that have quadruplex/duplex were shown to bind the fibrinogen-recognition exosite at the base of the active site cleft. The ligand inhibits thrombin-catalyzed clot formation in vitro (Tasset et al., 1997). Tasset et al. (1997) showed that a 15-mer containing quadruplex motif from the previous ssDNA inhibitor binds to the active cleft. Although not wanting to be bound by theory, such structural features may be important in metallo-β-lactamase inhibition as well. Although not wanting to be bound by theory, the aptamer compounds described in this invention can serve as lead compounds for a new generation of highly effective metallo-β-lactamase inhibitors.

These compositions and methods described herein are by no means all-inclusive, and further methods to suit the specific application will be apparent to the ordinary skilled artisan. The scope of the ligands covered by this invention extends to all nucleic acid ligands of lactamase and metallo-lactamases. Moreover, the effective amount of the compositions can be further approximated through analogy to compounds known to exert the desired effect.

What is claimed is:

1. A composition of matter comprising a nucleic acid ligand with SEQID# 4.

2. The composition of claim 1, wherein the nucleic acid ligand inhibits a lactamase.

3. The composition of claim 2, wherein the lactamase comprises a class B lactamase.

4. The composition of claim 3, wherein the class B lactamase comprises a metallo-β-lactamase.

5. The composition of claim 4, wherein the metallo-lactamase comprises a *B. cereus* 5/B/6 metallo-β-lactamase.

* * * * *

```
                              SEQUENCE LISTING

<160> NUMBER OF SEQ ID NOS: 6

<210> SEQ ID NO 1
<211> LENGTH: 16
<212> TYPE: DNA
<213> ORGANISM: artificial sequence
<220> FEATURE:
<223> OTHER INFORMATION: A 16 mer with a NdeI restriction site for
      SELEX.

<400> SEQUENCE: 1
gcgccatatg cgcgcg                                                        16

<210> SEQ ID NO 2
<211> LENGTH: 15
<212> TYPE: DNA
<213> ORGANISM: artificial sequence
<220> FEATURE:
<223> OTHER INFORMATION: A 15 mer with a SecI restriction site for
      SELEX.

<400> SEQUENCE: 2
cgcgagctcc gcgcg                                                         15

<210> SEQ ID NO 3
<211> LENGTH: 30
<212> TYPE: DNA
<213> ORGANISM: artificial sequence
<220> FEATURE:
<223> OTHER INFORMATION: This is the aptamer sequence after 16 rounds of
      SELEX.
<220> FEATURE:
<221> NAME/KEY: misc_feature
<222> LOCATION: (2)..(2)
<223> OTHER INFORMATION: n is A or T or G or C
<220> FEATURE:
<221> NAME/KEY: misc_feature
<222> LOCATION: (4)..(4)
<223> OTHER INFORMATION: n is A or T or G or C
<220> FEATURE:
<221> NAME/KEY: misc_feature
<222> LOCATION: (6)..(6)
<223> OTHER INFORMATION: N is A or T or G or C
<220> FEATURE:
<221> NAME/KEY: misc_feature
<222> LOCATION: (7)..(7)
<223> OTHER INFORMATION: N is A or T or G or C
<220> FEATURE:
<221> NAME/KEY: misc_feature
<222> LOCATION: (8)..(8)
<223> OTHER INFORMATION: N is A or T or G or C
<220> FEATURE:
<221> NAME/KEY: misc_feature
<222> LOCATION: (11)..(11)
<223> OTHER INFORMATION: N is A or T or G or C
<220> FEATURE:
<221> NAME/KEY: misc_feature
<222> LOCATION: (12)..(12)
<223> OTHER INFORMATION: N is A or T or G or C
<220> FEATURE:
<221> NAME/KEY: misc_feature
<222> LOCATION: (13)..(13)
<223> OTHER INFORMATION: N is A or T or G or C
```

```
<220> FEATURE:
<221> NAME/KEY: misc_feature
<222> LOCATION: (15)..(15)
<223> OTHER INFORMATION: N is A or T or G or C
<220> FEATURE:
<221> NAME/KEY: misc_feature
<222> LOCATION: (17)..(17)
<223> OTHER INFORMATION: N is A or T or G or C
<220> FEATURE:
<221> NAME/KEY: misc_feature
<222> LOCATION: (18)..(18)
<223> OTHER INFORMATION: N is A or T or G or C
<220> FEATURE:
<221> NAME/KEY: misc_feature
<222> LOCATION: (20)..(20)
<223> OTHER INFORMATION: N is A or T or G or C
<220> FEATURE:
<221> NAME/KEY: misc_feature
<222> LOCATION: (21)..(21)
<223> OTHER INFORMATION: N is A or T or G or C
<220> FEATURE:
<221> NAME/KEY: misc_feature
<222> LOCATION: (25)..(25)
<223> OTHER INFORMATION: N is A or T or G or C
<220> FEATURE:
<221> NAME/KEY: misc_feature
<222> LOCATION: (26)..(26)
<223> OTHER INFORMATION: N is A or T or G or C
<220> FEATURE:
<221> NAME/KEY: misc_feature
<222> LOCATION: (27)..(27)
<223> OTHER INFORMATION: N is A or T or G or C
<220> FEATURE:
<221> NAME/KEY: misc_feature
<222> LOCATION: (28)..(28)
<223> OTHER INFORMATION: N is A or T or G or C

<400> SEQUENCE: 3
ancnannntt nnntngnngn ncatnnnnaa                                        30

<210> SEQ ID NO 4
<211> LENGTH: 30
<212> TYPE: DNA
<213> ORGANISM: artificial sequence
<220> FEATURE:
<223> OTHER INFORMATION: This is the aptamer 30-mer sequence after 21
      rounds of SELEX.

<400> SEQUENCE: 4
aaccaaactt ggatcggtgc acatgtcgaa                                        30

<210> SEQ ID NO 5
<211> LENGTH: 10
<212> TYPE: DNA
<213> ORGANISM: artificial sequence
<220> FEATURE:
<223> OTHER INFORMATION: This is a 10 mer that contains a specific stem
      loop structure
<220> FEATURE:
<221> NAME/KEY: stem_loop
<222> LOCATION: (1)..(10)

<400> SEQUENCE: 5
ccaaacttgg                                                              10

<210> SEQ ID NO 6
<211> LENGTH: 61
<212> TYPE: DNA
<213> ORGANISM: artificial sequence
```

-continued

```
<220> FEATURE:
<223> OTHER INFORMATION: the aptamer (61-mer)

<400> SEQUENCE: 6
gcgccatatg cgcgcgaacc aaacttggat cggtgcacat gtcgaacgcg cggagctcgc    60
g                                                                    61
```